US009717826B2

(12) United States Patent
Dugan et al.

(10) Patent No.: US 9,717,826 B2
(45) **Date of Patent: *Aug. 1, 2017**

(54) COATINGS FOR PREVENTING BALLOON DAMAGE TO POLYMER COATED STENTS

(71) Applicant: ABBOTT CARDIOVASCULAR SYSTEMS INC., Santa Clara, CA (US)

(72) Inventors: Stephen R. Dugan, San Francisco, CA (US); Jessica R. Desnoyer, Bedford, MA (US); Stephen D. Pacetti, San Jose, CA (US); Bozena Maslanka, Santa Cruz, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/099,515

(22) Filed: Apr. 14, 2016

(65) Prior Publication Data

US 2016/0228618 A1 Aug. 11, 2016

Related U.S. Application Data

(60) Continuation of application No. 14/311,174, filed on Jun. 20, 2014, now Pat. No. 9,345,815, which is a (Continued)

(51) Int. Cl.

*A61F 2/06* (2013.01)
*A61L 31/10* (2006.01)

(Continued)

(52) U.S. Cl.

CPC .............. *A61L 31/10* (2013.01); *A61F 2/844* (2013.01); *A61F 2/86* (2013.01); *A61F 2/915* (2013.01);

(Continued)

(58) Field of Classification Search

CPC . A61F 2/958; A61F 2/86; A61L 31/08; A61L 31/10; A61L 31/14; A61L 31/16;

(Continued)

(56) References Cited

U.S. PATENT DOCUMENTS

| | | |
|---|---|---|
| 4,304,767 A | 12/1981 | Heller et al. |
| 4,733,989 A | 3/1988 | Harriett |

(Continued)

FOREIGN PATENT DOCUMENTS

| | | |
|---|---|---|
| EP | 0778250 | 11/1996 |
| EP | 1247537 | 10/2002 |
| WO | WO 94/09010 | 4/1994 |

OTHER PUBLICATIONS

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, Nov. 1, 2001, pp. 1570-1576.

(Continued)

*Primary Examiner* — Katherine Rodjom

(74) *Attorney, Agent, or Firm* — Squire Patton Boggs (US) LLP

(57) ABSTRACT

A medical assembly is disclosed comprises a stent and a catheter having a balloon, wherein the coefficient of friction and/or the adhesion at the stent/balloon interface are reduced.

12 Claims, 26 Drawing Sheets

Related U.S. Application Data division of application No. 10/816,072, filed on Mar. 31, 2004, now Pat. No. 8,778,014.

(51) Int. Cl.

| | |
|---|---|
| ***A61F 2/86*** | (2013.01) |
| ***A61F 2/958*** | (2013.01) |
| ***A61L 31/14*** | (2006.01) |
| ***A61L 31/16*** | (2006.01) |
| ***A61L 29/14*** | (2006.01) |
| ***A61F 2/844*** | (2013.01) |
| ***A61F 2/915*** | (2013.01) |

(52) U.S. Cl.

CPC .............. *A61F 2/958* (2013.01); *A61L 29/14* (2013.01); *A61L 31/14* (2013.01); *A61L 31/16* (2013.01); *A61F 2002/91533* (2013.01); *A61F 2002/91583* (2013.01); *A61L 2300/426* (2013.01); *A61L 2400/10* (2013.01); *A61L 2420/02* (2013.01); *A61L 2420/08* (2013.01)

(58) Field of Classification Search

CPC . A61L 29/14; A61L 2400/10; A61L 2300/452

See application file for complete search history.

(56) References Cited

U.S. PATENT DOCUMENTS

| | | | |
|---|---|---|---|
| 5,581,387 A | 12/1996 | Cahill | |
| 5,637,113 A | 6/1997 | Tartaglia et al. | |
| 5,646,160 A | 7/1997 | Morris et al. | |
| 5,861,387 A | 1/1999 | Labrie et al. | |
| 6,015,815 A | 1/2000 | Mollison | |
| 6,254,634 B1 | 7/2001 | Anderson et al. | |
| 6,329,386 B1 | 12/2001 | Mollison | |
| 6,369,039 B1 | 4/2002 | Palasis et al. | |
| 6,503,538 B1 | 1/2003 | Chu et al. | |
| 6,541,116 B2 | 4/2003 | Michal et al. | |
| 6,585,764 B2 | 7/2003 | Wright et al. | |
| 6,607,598 B2 | 8/2003 | Schwarz et al. | |
| 6,703,040 B2 | 3/2004 | Katsarava et al. | |
| 6,890,546 B2 | 5/2005 | Mollison et al. | |
| 6,896,965 B1 | 5/2005 | Hossainy | |
| 6,939,376 B2 | 9/2005 | Shulze et al. | |
| 7,055,237 B2 | 6/2006 | Thomas | |
| 7,208,010 B2 | 4/2007 | Shanley et al. | |
| 7,282,216 B2 | 10/2007 | Costantino et al. | |
| 7,357,942 B2 | 4/2008 | Burke et al. | |
| 7,378,105 B2 | 5/2008 | Burke et al. | |
| 7,611,532 B2 | 11/2009 | Bates et al. | |
| 7,727,275 B2 | 6/2010 | Betts et al. | |
| 7,875,282 B2 | 1/2011 | Falotico et al. | |
| 7,875,283 B2 | 1/2011 | Hossainy et al. | |
| 7,959,999 B2 | 6/2011 | Prabhu | |
| 8,192,752 B2 | 6/2012 | Tang et al. | |
| 8,303,609 B2 | 11/2012 | Lentz et al. | |
| 8,551,512 B2 | 10/2013 | Hossainy et al. | |
| 8,685,428 B2 | 4/2014 | Zhang et al. | |
| 8,778,014 B1 | 7/2014 | Dugan et al. | |
| 9,114,198 B2 | 8/2015 | Hossainy et al. | |
| 9,345,815 B2 * | 5/2016 | Dugan | A61F 2/86 |
| 2002/0082679 A1 | 6/2002 | Sirhan et al. | |
| 2002/0165601 A1 | 11/2002 | Clerc | |
| 2003/0033007 A1 | 2/2003 | Sirhan et al. | |
| 2003/0050692 A1 | 3/2003 | Sirhan et al. | |
| 2003/0170287 A1 | 9/2003 | Prescott | |
| 2004/0170685 A1 | 9/2004 | Carpenter et al. | |
| 2004/0199241 A1 | 10/2004 | Gravett et al. | |
| 2005/0049693 A1 | 3/2005 | Walker | |
| 2005/0125054 A1 | 6/2005 | Bhat et al. | |
| 2005/0203612 A1 | 9/2005 | Bhat et al. | |
| 2014/0303708 A1 | 10/2014 | Dugan et al. | |

OTHER PUBLICATIONS

De Lezo et al., *Intracoronary Ultrasound Assessment of Directional Coronary Atherectomy: Immediate and Follow-Up Findings*, JACC vol. 21, No. 2, Feb. 1993, pp. 298-307.

Moreno et al., *Macrophage Infiltration Predicts Restenosis After Coronary Intervention in Patients with Unstable Angina*, Circulation, vol. 94, No. 12, Dec. 12, 1996, pp. 3098-3102.

Oikawa et al., Mechanisms of Acute Gain and Late Lumen Loss After Atherectomy in Different Preintervention Arterial Remodeling Patterns, *The Am. J. of Cardilogy*, vol. 89, Mar. 1, 2002, pp. 505-510.

Scully et al., *Effect of a heparan sulphate with high affinity for antithrombin III upon inactivation of thrombin and coagulaton Factor Xa*, Biochem J. 262, Apr. 1989, pp. 651-658.

Virmani et al., *Lessons From Sudden Coronary Death: a Comprehensive Morphological Classification Scheme for Atherosclerotic Lesions*, Arterioscler Thromb Vasc Biol., May 2000, pp. 1262-1275.

* cited by examiner (a)

(b)

(c)

COATINGS FOR PREVENTING BALLOON DAMAGE TO POLYMER COATED STENTS

CROSS-REFERENCE TO RELATED APPLICATIONS

This application is a continuation of U.S. patent application Ser. No. 14/311,174, filed on Jun. 20, 2014, published as US 2014-0303708 A1 on Oct. 9, 2014, and issuing as U.S. Pat. No. 9,345,815 B2 on May 24, 2016, which is a division of U.S. patent application Ser. No. 10/816,072, filed on Mar. 31, 2004, and issuing as U.S. Pat. No. 8,778,014 on Jul. 15, 2014, both of which are incorporated by reference herein in their entirety, expressly including any drawings, and both are incorporated by reference for all purposes.

BACKGROUND

Field of the Invention

This invention relates to the field of polymer coated stents. More specifically, this invention relates to coating treatments for polymer coated stents and delivery balloons to prevent or reduce deployment damage caused by the balloon to a polymer coated stent.

Description of the State of the Art

Stents are being modified to provide drug delivery capabilities. A polymeric carrier, impregnated with a drug or therapeutic substance is coated on the surfaces of a stent. The conventional method of coating is by applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. The dipping or spraying of the composition onto the stent can result in a complete coverage of all stent surfaces, i.e., both luminal (inner) and abluminal (outer) surfaces, with a coating. However, having a coating on the luminal surface of the stent can have a detrimental impact on the stent's deliverability as well as the coating's mechanical integrity.

Briefly, an inflatable balloon of a catheter assembly is inserted into a hollow bore of a stent. The stent is securely crimped on the balloon. The balloon is inflated to implant the stent, deflated, and then withdrawn out from the bore of the stent. A polymeric coating can increase the coefficient of friction between the stent and the balloon of a catheter assembly on which the stent is crimped for delivery. Additionally, some polymers have a "sticky" or "tacky" consistency. If the polymeric material either increases the coefficient of friction or adherers to the catheter balloon, the effective release of the stent from the balloon after deflation can be compromised. If the stent coating adheres to the balloon, the coating, or parts thereof, can be pulled off the stent during the process of deflation and withdrawal of the balloon following the placement of the stent. Adhesive, polymeric stent coatings can also experience extensive balloon sheer damage post-deployment, which could result in a thrombogenic stent surface and possible embolic debris. The stent coating can stretch when the balloon is expanded and may delaminate as a result of such shear stress. Accordingly, there is a need to eliminate or minimize damage caused to a coating of a stent by the delivery balloon.

SUMMARY

A medical assembly is provided comprising a stent having a polymer coating and a catheter having a balloon supporting the polymer coated stent, a surface of the polymer coating and/or a surface of the balloon being modified so as to provide a lower kinetic coefficient of friction and/or adhesion at the polymer coating surface/balloon surface interface as compared to the kinetic coefficient of friction and/or adhesion of unmodified surface or surfaces so as to prevent or minimize coating damage to the polymer coating during expansion, deflation and/or withdrawal of the balloon.

DETAILED DESCRIPTION

Terms and Definitions

Figure 1:
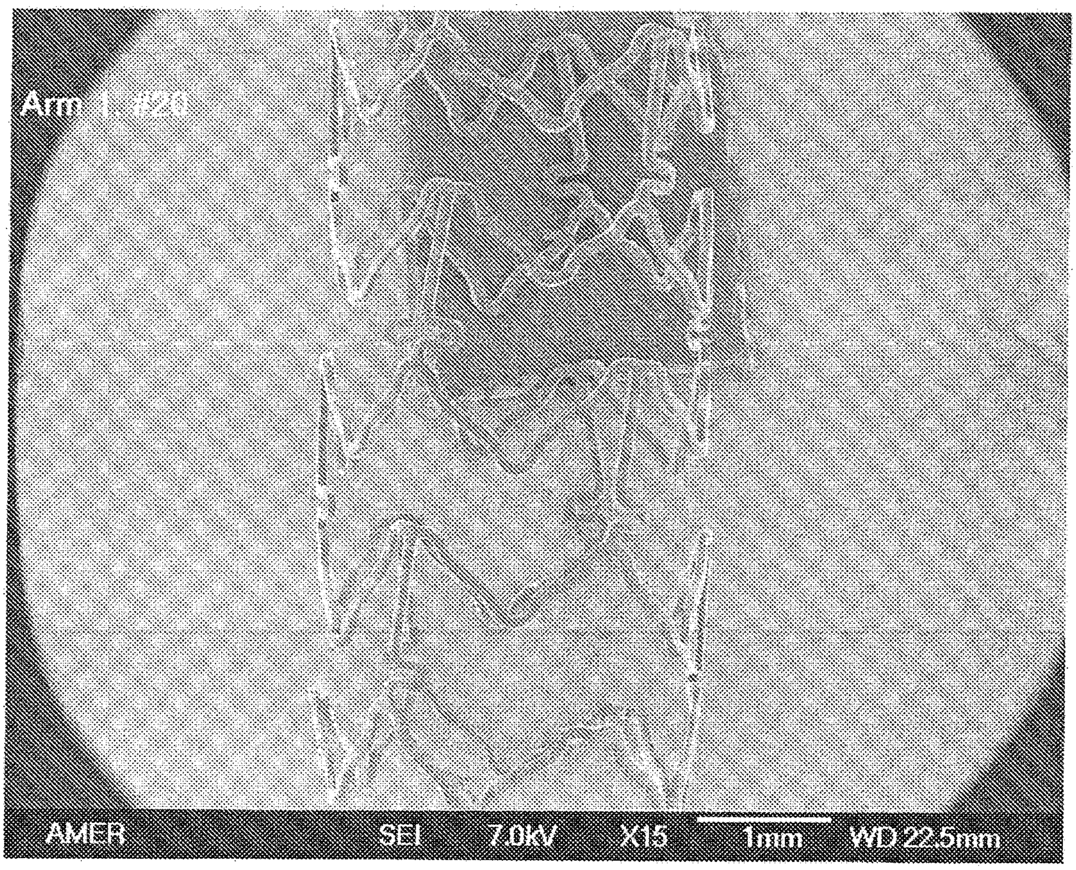
FIGS. 1-48 are the microphotographs showing stent coatings formed and tested according to the examples provided herein.

The following terms and definitions apply:

The term "kinetic coefficient of friction" is defined by its conventional definition as is understood to one having ordinary skill in the art such as the ratio of the friction to the perpendicularly applied pressure. Friction is developed when two contacting surfaces move relative to each other.

The term "static coefficient of friction" is defined by its conventional definition as is understood to one having ordinary skill in the art such as the ratio of the limiting friction to the perpendicularly applied pressure. The limiting friction exists when two contacting surfaces are stationary relative to each other.

The term "adhesion" refers to a tendency of the surfaces of the balloon and the coated stent to stick together, such as to cause an undesirable amount of the coating to delaminate, detach or peel off of the stent or as to form an undesirable coating defect during expansion, deflation, and/or withdrawal of the balloon.

The term "blocking agent" refers to compounds preventing or at least reducing the adhesion between the stent and the balloon at the stent/balloon interface. The blocking agent can also serve as a lubricant, reducing the kinetic coefficient of friction between the stent and the balloon at the stent/balloon interface.

EMBODIMENTS OF THE INVENTION

At least two factors can contribute to cause damage to a stent coating. The first factor is the friction between the inner surface of a coated stent and the surface of a delivery catheter balloon that is used for implanting the stent when the two surfaces move relative to each other. The second factor is adhesion between a coated stent and the balloon. To reduce or eliminate the damage to the stent coating caused by these two factors, the surface(s) of the balloon and/or of the coated stent can be modified. The surface of the coated stent can be both the inner and outer surfaces of the coated stent. Preferably, only the inner surface of the coated stent, and in some cases a fraction of the side walls of the struts, needs modification. The purpose of such modification is to reduce the kinetic coefficient of friction at the stent/balloon interface and/or to reduce the adhesion between the two surfaces.

According to one embodiment of the present invention, the kinetic coefficient of friction at the interface for the modified surface(s) of the balloon and/or the stent can be reduced as compared to the kinetic coefficient of friction at the interface of an unmodified surface(s), by about 1% to less than about 100%, about 5% to about 95%, about 10% to about 90%, about 25% to about 75%, for example, by about 40%. In some embodiments, the static coefficient of friction between the stent and the balloon for the modified surface(s) can remain substantially the same as compared to the unmodified surface(s).

The kinetic coefficient of friction can be measured by any method commonly used by those having ordinary skill in the art. For example, an inclined plane test conducted in an aqueous solution (e.g., de-ionized water) at a temperature of about 37° C. can be used. A test article can be placed on a horizontal flat surface. With the test article placed on the flat surface, one end of the flat surface can be slowly raised until the motion of the test article is detected. The angle of the flat surface at which the movement of the test article can be visually observed can be measured, for example using scale, protractor, or linear measuring scheme. The coefficient of friction may be calculated by taking the tangent of that angle. By way of example, a sheet of PEBAX® 72D polymer can be used as the flat surface. A rigid substrate coated with PEBAX® 72D or an extruded strip of PEBAX® 72D attached to a rigid substrate can be used. PEBAX® is a trade name of a family of polyether-block-co-polyamide polymers available from Atofina Chemicals of Philadelphia, Pa. With the flat surface horizontal and immersed in the 37° C. water bath, the coated stent can be placed onto the flat surface. Then the angle can be increased until the stent starts moving. The angle at which the movement of the stent is visually detected can be measured. The coefficient of friction may be calculated using this angle.

By way of another example, a flat, rigid substrate can be coated with a polymeric coating, for example, by dipping or spraying. The coated substrate can be immersed in the 37° C. water bath. A block of PEBAX® 72D can serve as the test article, which can be placed onto the flat surface. Then the angle can be increased until the PEBAX® block starts moving. The angle at which the movement of the block is visually detected can be measured. A coefficient of friction may be calculated by taking the tangent of that angle.

According to another embodiment of the present invention, the adhesion between the modified surface(s) of the balloon and/or the stent can be reduced, as compared to the adhesion of an unmodified surface(s), by at least 5%, 10%, 20%, or alternatively by at least 30%. In one embodiment adhesion is reduced by about 50% to about 100%, including reduction by about 60%, 70%, 80% or about 90%. In some embodiments, the static coefficient of friction between the modified surfaces remains substantially the same as between the unmodified surfaces. Adhesion can be measured using any standard method known to those having ordinary skill in the art.

To provide drug delivery capabilities, a coating can be formed on at least a portion of the stent surface. The stent coating can include a drug-polymer layer (also referred to as “reservoir” or “reservoir layer”) and in some embodiments a topcoat layer. The reservoir layer can serve as a matrix for the sustained release of the drug. The reservoir layer can be applied directly onto at least a portion of the stent surface. Optionally, a primer layer can be applied on at least a portion of the stent surface to improve the adhesion of the drug-polymer layer to the stent. The topcoat layer, which can be essentially free from any drugs, can be applied over at least a portion of the reservoir layer to serve as a rate limiting membrane which helps to control or reduce the rate of release of the drug. For the topcoat layer, some drug may migrate into the layer subsequent to the deposition of the layer. The topcoat layer, if used, is the outermost layer of the stent coating. If the topcoat layer is not used, then the reservoir layer is the outermost layer of the stent coating. Other intermediary layers can be formed between any of the aforementioned three layers.

Each of the primer, reservoir, and the topcoat layers can be formed on the stent by dissolving a polymer or a blend of polymers in a solvent, or a mixture of solvents, and applying the resulting polymer solution on the stent by any commonly used technique, such as spraying or immersing the stent in the solution. To incorporate a drug into the reservoir layer, the drug in a form of a solution can be combined with the polymer solution.

Instead of introducing the drug in a solution, the drug can be introduced as a colloidal system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art will select the suitable solvent to form the solvent phase of the suspension, as well as the quantity of the drug to be dispersed in the solvent phase. The suspension can be mixed with a polymer solution and the mixture can be applied on the stent as described above.

To reduce a kinetic coefficient of friction at the stent/balloon interface, and/or the adhesion between the two surfaces, in some embodiments a blocking agent can be deposited on or over the surface of the stent coating. Depending on the type of blocking agent used, a sufficient quantity needs to be applied so as to reduce friction and/or adhesion. Some blocking agents may incidentally seep into the coating. Accordingly, “on the surface” or “over the surface” is defined by its conventional meaning as well as to include blocking agent migration into the polymeric coating. The application of a blocking agent can also be beneficial over a surface of a bare stent without any polymeric or other types of coating. Even over a bare stent, the agents can assist in better delivery of the stent. In some embodiments, a blocking agent can be incorporated, blended or embedded within the stent coating. The blocking agent can also be conjugated, linked or bonded with a polymer of the stent coating. The conjugation, linkage or bonding can be direct or via a linking or intermediary agent. In some embodiments, the blocking agent should be of a type that allows the blocking agent to migrate to the upper region of the stent coating or the coating/air interface. Otherwise, or in addition to having the propensity to surface bloom, the process employed should cause the extraction of the blocking agent to the upper most region of the surface or to the coating/air interface. If conjugated, linked or bonded to a polymer of the coating, rotation of the polymer during the coating process such that the blocking agent is positioned on top is preferable. The blocking agent can also be conjugated, bonded or linked to the outer surface of the coating. A sufficient amount of blocking agent needs to be used so as to achieve the intended reduction in friction and/or adhesion. Alternatively the blocking agent must be of a type that allows for the reduction in friction and adhesion, regardless of the amount used. In another alternative, the process can allow for a sufficient amount to blocking agent to migrate so that the intended goals of the invention are met.

In some embodiments, in lieu of or in addition to the use of a blocking agent, a low adhesion polymer can be used to form the outermost layer of the coating or the outermost layer can be treated with low adhesion type polymers. Treatment of the outer layer or topcoat layer can include surface treatment or intermixing or blending of the outer layer or top coat layer with a low adhesion type polymer. As with the blocking agent, with surface treatment, incidental migration, seepage or blending of the low adhesion polymer into the stent coating may occur. A low adhesion polymer can also be bonded, linked or conjugated to the polymer of the stent coating. Similar to that of a blocking agent, a low adhesion polymer could of the type that migrates, when intermixed, to the upper most surface of the outer most layer or to the coating/air interface. If bonded, linked or conjugated, the low adhesion polymer can shift or rotate on top of the polymer to which it is bonded.

In some embodiments, a blocking agent can be disposed on or over the balloon of a catheter prior to the crimping of the stent on the balloon. The crimping process should not affect the properties of the blocking agent or to remove or wash away the blocking agent. A coating can be formed on the balloon made from the blocking agent if a sufficient amount of the agent is applied to the balloon under the appropriate process parameters. In some embodiments, the blocking agent can be intermixed, blended, conjugated, linked or bonded with a polymer and applied to the balloon. The same principles, such as surface blooming discussed with the stent, are equally applicable with a balloon. The blocking agent can also be bonded, linked or conjugated to the surface of the balloon. In some embodiments, a low adhesion coating, with or without a blocking agent can be applied to the balloon surface prior to the crimping of the stent. The balloon can also be made from a material or include a layer of material having characteristics that achieve the intended reduction in friction and/or adhesion.

In some embodiments, any combination of the above methods can be used. To illustrate, a blocking agent can be deposited both over the stent coating and the balloon, or a stent can be coated with a coating, the outermost layer of which comprises a low adhesion polymer, and a balloon can be coated with a coating comprising a blocking agent. The blocking agent can be deposited by, for example, spraying or swabbing. Preferably, for the stent, about 0.05 μg to about 5 μg of the blocking agent can be deposited per 1 $mm^2$ of surface area, for example, between about 0.1 μg/$mm^2$ and about 1 μg/$mm^2$, such as about 0.5 μg/$mm^2$. Preferably, about 0.5 μg to about 2 μg of the blocking agent can be deposited per 1 $mm^2$ of the surface of the balloon, for example, between about 0.8 μg/$mm^2$ and about 1.2 μg/$mm^2$, such as about 1 μg/$mm^2$. If the balloon include pleats or folded regions, it may be desirable to coat underneath the creases. This can be achieved by swabbing into the creases or inflation of the balloon to open up the creases. As for incorporation of the blocking agent in the coating, about 1 mass % to about 50 mass %, for example, about 2 mass % of agent can be included in the dry stent or balloon coating.

In one embodiment, a dry powder form of the blocking agent can be applied to the stent or balloon. Alternatively, a blocking agent can be dissolved in a solvent and sprayed directly onto the surface. The blocking agent can also be mixed with a solution of a polymer, followed by applying the composition on the stent or balloon. After the composition has been applied, the solvent in the combined solution is expected to extract the blocking agent and to cause the migration of the blocking agent to the surface of the coating. Once the blocking agent has reached the surface of the stent coating, it can serve to reduce the friction and/or adhesion on the stent/balloon interface. To facilitate the process of extraction, it is preferred that between the polymer and the blocking agent forming the combined solution, the blocking agent should be more readily soluble in the solvent of the composition.

Some blocking agents are water soluble and can therefore be released into the blood stream. Such blocking agents need to be biologically compatible and not adversely compromise the biological response of the body to the stent or the coating. Examples of blocking agents that can be used include sucrose, poly(ethylene glycol)(PEG), poly(ethylene oxide)(PEO), solvent-soluble fluorinated polymers, block copolymers of bioabsorbable polymers with perfluorinated end chains, SILWET® surfactants (available from Union Carbide Corp.), FLUORAD® surfactants (available from 3M Co.), non-ionic surfactants having alkyl, perfluorinated, or silicone chains, fatty alcohols, waxes, fatty acid salts, mono-, di-, and triglycerides, cholesterol, lecithin, dextran, dextrin, esters and ethers of cellulose, e.g., carboxymethyl cellulose and cellulose acetate, cellulosics, maltose, glucose, mannose, trehalose, sugars, poly(vinyl alcohol)(PVA), poly (2-hydroxyethyl methacrylate), poly(N-vinyl-pyrrolidone) (PVP), silicone oil, paraffins, paraffin oil, and inorganic powders, such as talcum powder, calcium salt powder, and magnesium salt powder. Other carbohydrates such as starches and dextrose can also serve as a blocking agent. Hyaluronic acid can also be used to reduce friction and/or adhesion. In some embodiments, the blocking agent incorporated into the stent coating can simultaneously serve as a drug. Examples of such dual-function blocking agents include steroids, clobetasol, estradiol, dexamethasone, paclitaxel, rapamycin, (available from Wyeth Pharmaceuticals of Madison, N.J., under the generic name sirolimus), and structural derivative or functional analogs of rapamycin, 40-O-(2-hydroxy)ethyl-rapamycin (known by the generic name of everolimus available from Novartis), 40-O-(3-hydroxy)propyl-rapamycin, 40-O-[2-(2-hydroxy)ethoxy] ethyl-rapamycin, and 40-O-tetrazole-rapamycin, and drugs with an octanol/water partition coefficient greater than 100. In some embodiments of the invention, the blocking agent can exclude any of the aforementioned substances. For example, the blocking agent can consist of glucose, mannose, silicone oil, paraffins, paraffin oil, and inorganic powders, such as talcum powder, calcium salt powder, and magnesium salt powder with the provision that the blocking agent is not paclitaxel, rapamycin, estradiol or any one of the aforementioned substances. With the use of these substances, most particularly the listed drugs, again, there must be a sufficient amount of the drug disposed on the surface or located at the coating/air interface region so as to be able to reduce the friction and/or adhesion. Simple blends of these substances, most particularly the drugs, with a polymer drug delivery matrix may be insufficient. For example, a stent coating including a blend of a polymer or polymers with rapamycin, clobetasol, estradiol, dexamethasone, or paclitaxel may not be sufficient to reduce the friction and/or adhesion. These substances must be present at sufficient amount on the surface of the stent coating or be processed such that the agents migrate to the coating/air interface at a sufficient level so as to achieve the goals of the present invention.

Polymers capable of reducing friction and/or adhesion are referred to as "low adhesion polymers." These types of polymers can be deposited on the stent coating or on the balloon by a variety of different applications. As for balloons, plasma polymerization may be favorable so as to produce a thin layer of the coating. The balloon coating has to be thick enough to affect the surface properties but not affect balloon flexibility or compliance. In some embodiments, the thickness can be in submicron range. It can be for example 0.5 microns thick. Optionally, one or more blocking agents can be blended with a low adhesion polymer or be deposited on the surface of these polymers. Low adhesion polymers can be fully or partially fluorinated or non-fluorinated. Examples of low adhesion fluorinated polymers that can be used include poly(tetrafluoro ethylene) (PTFE), poly (vinylidene fluoride)(PVDF), and poly(vinylidene fluoride-co-hexafluoropropene) (PVDF-HFP). Various brands of PTFE can be used, including any products of TEFLON® family available from E. I. DuPont de Nemours of Wilmington, Del. Various brands of PVDF-HFP known as SOLEF® family of products, available from Solvay Fluoropolymers, Inc. of Houston, Tex., can be used, for example, SOLEF® 21508 having about 85 mass % of vinylidene fluoride-derived units and about 15 mass % of hexafluoro propene-derived units. PVDF-HFP is also available from Atofina Chemicals of Philadelphia, Pa., under the trade name KYNAR®. Examples of low adhesion non-fluorinated polymers that can be used include poly(n-butyl methacrylate)(PBMA), poly(methyl methacrylate)(PMMA), poly (ethyl methacrylate)(PEMA), polycarbonate, polystyrene and poly(butyleneterephthalate-co-ethylene glycol) (PBT-PEG). In some embodiments a family of PBT-PEG known as POLYACTIVE® can be used. POLYACTIVE® is a trade name of a PBT-PEG group of products and is available from IsoTis Corp. of Holland. In various brands of POLYACTIVE®, the ratio between the units derived from ethylene glycol and the units derived from butylene terephthalate can be between about 0.67:1 and about 9:1. The molecular weight of the units derived from ethylene glycol can be between about 300 and about 4,000 Daltons. In some embodiments, any of the aforementioned polymers can be excluded from the practice of the present invention. For example, a stent coating or balloon can be coated on the outermost surface with POLYACTIYE® with the provision that the low adhesion polymer is not PBMA.

With respect to the stent coating, examples of some polymers that can be used for fabricating the primer, reservoir, and/or the topcoat layers include poly(ester amides), poly(ethylene-co-vinyl alcohol) (known also under a trade name EVAL®, for example, EVAL® having a molar content of ethylene-derived units of more than about 44%), poly (hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), poly(glycerol-sebacate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, diisocyanate-based block copolymers, such as ELASTEON® (a trade name of the block copolymer of methylene diphenyl diisocyanate, 1,4-butanediol, polyhexamethyleneglycol, and a carbinol terminated polydimethylsiloxane, manufactured by AorTech Biomaterials Co. of Chatswood, Australia), silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

Representative examples of some solvents that can be used in the practice of the invention include N,N-dimethylacetamide (DMAC), N,N-dimethylformamide (DMF), or dimethylsulfoxide (DMSO), cyclohexanone, tethrahydrofuran (THF), xylene, toluene, acetone, i-propanol, methyl ethyl ketone, propylene glycol monomethyl ether, methyl butyl ketone, ethyl acetate, n-butyl acetate, chloroform, trichloroethane, trichloroethylene, ethanol, methanol, and dioxane. Some solvent mixtures can be used as well. Representative examples of the mixtures include:

(1) DMAC and methanol (e.g., 50:50 by mass mixture);

(2) water, i-propanol, and DMAC (e.g., 10:3:87 by mass mixture);

(3) i-propanol, and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. 50:50 by mass mixture); and (6) acetone, FLUX REMOVER® AMS, and xylene (e.g., 10:50:40 by mass mixture).

FLUX REMOVER® AMS is the trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer or blend of polymers being dissolved.

Generally speaking, the active agent or the drug can include any substance capable of exerting a therapeutic, diagnostic or prophylactic effect for the patient. The drug may include small molecule drugs, peptides, proteins, oligonucleotides, and the like. In addition to drugs that are also blocking agents, mentioned above, examples of other drugs that can be used include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, and tacrolimus.

The embodiments of the present invention have been described with reference to a stent, such as a balloon expandable or self-expandable stent. The embodiments are, however, not limited to stents and may have a useful application with a variety of other medical devices and implantable prostheses. Examples of medical device, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE® and ENDOTAK®, available from Guidant Corporation). The underlying structure of the device can be of virtually any design. The device can be made of a metallic material or an alloy such as, but not limited to, cobalt-chromium alloys (e.g., ELGILOY®), stainless steel (316L), "MP35N," "MP20N," ELASTINITE® (nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable, bioerodible, or biostable polymers can also be used with the embodiments of the present invention. For example the stent can be a completely bioabsorbable or bioerodible stent. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention can be further illustrated by the following set forth examples.

Example 1

A first composition was prepared by mixing the following components:

(a) about 2 mass % poly(benzyl ester amide) having an apparent weight-averaged molecular weight of about 90,000 Daltons; and (b) the balance, 200 proof ethanol (100% ethanol containing not more than trace amounts of water).

The first composition was applied onto the surface of bare 12 mm VISION® stents (available from Guidant Corporation) by spraying and dried to form a stent coating ("PEA coating"). A spray coater was used, having a 0.014 fan nozzle maintained at ambient temperature with a feed pressure of about 0.2 atm (about 3 psi) and an atomization pressure of about 1.3 atm (about 20 psi). About 20 μg of the wet coating was applied per pass. Between the passes, the coating was dried at about 80° C. for about 10 seconds. Following the last pass, the coating was baked at about 80° C. for about 30 minutes, yielding a dry coating. The dry coating contained about 300 μg of PEA.

A second composition was prepared by mixing the following components:

(a) about 3 mass % sucrose; and (b) the balance, water.

The second composition was sprayed over two separate stents, each coated with the PEA coating described above, using the spraying technique described above. About 6 μg of sucrose was applied on the first stent and about 64 μg of sucrose was applied on the other.

The coated stents were crimped on catheter balloons (12 mm VISION®) to form the stent/catheter assemblies, followed by electronic beam sterilization. The stent/catheter assemblies were then subjected to expansion according to the "Coated Stent Stimulated Use Test." The stent/catheter assemblies that included the following stents were tested:

(1) a stent having 6 μg of sucrose applied over the PEA coating;

(2) a stent having 64 μg of sucrose applied over the PEA coating; and (3) a PEA coated stent having no sucrose applied over the PEA coating (control stent).

According to the Stimulated Use Test, each coated stent was guided through a tortuous path and then deployed in a poly(vinyl alcohol) (PVA) lesion having approximate size of about 3 by 10 millimeters. The tortuous path and the lesion contained de-ionized water at about 37° C. To deploy the stents, a saline solution was used to apply pressure of about 16 atm to the balloon for about 1 minute, followed by deflating of the balloon and retraction of the catheter. After the catheter was retracted, de-ionized water was pumped through the tortuous path and the lesion for about 1 hour at a rate of about 50 milliliters per minute. Water was maintained at about 37° C.

Figure 2:
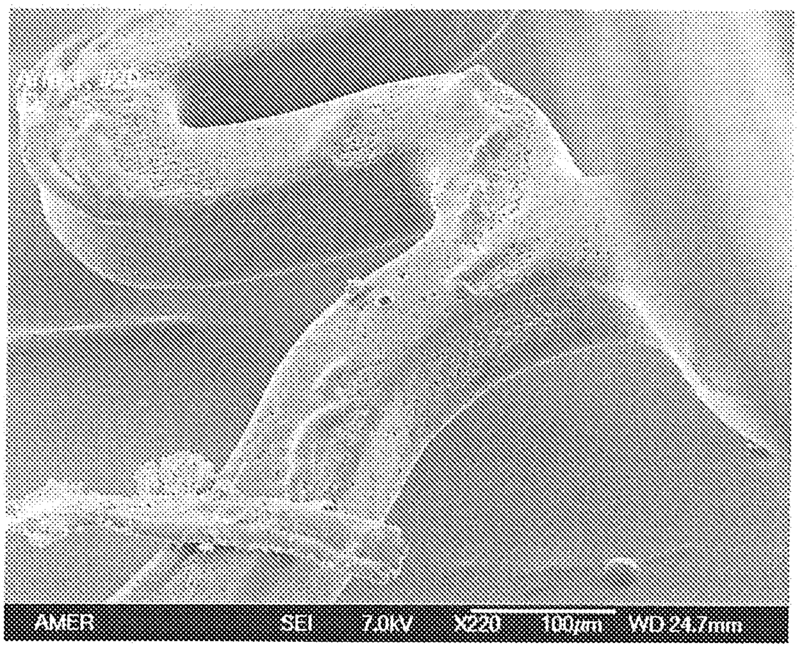
Figure 3:
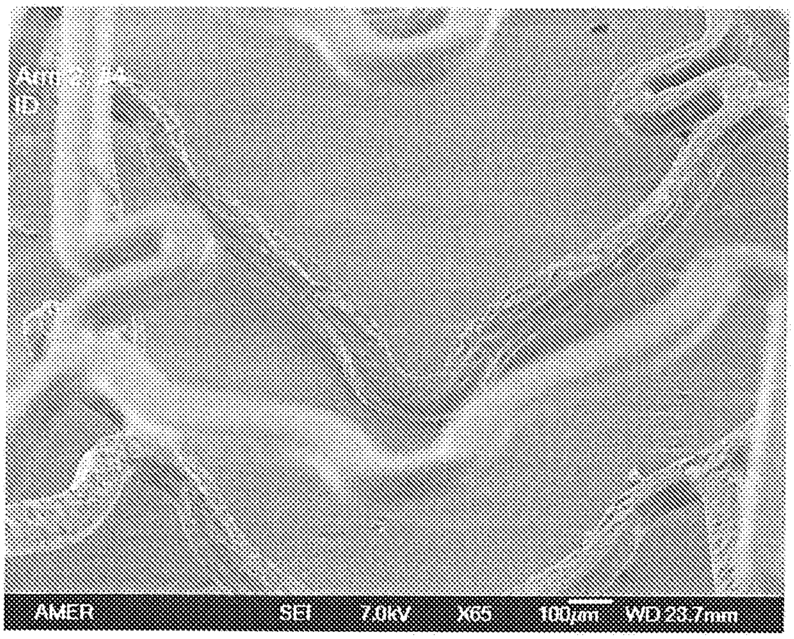
Figure 4:
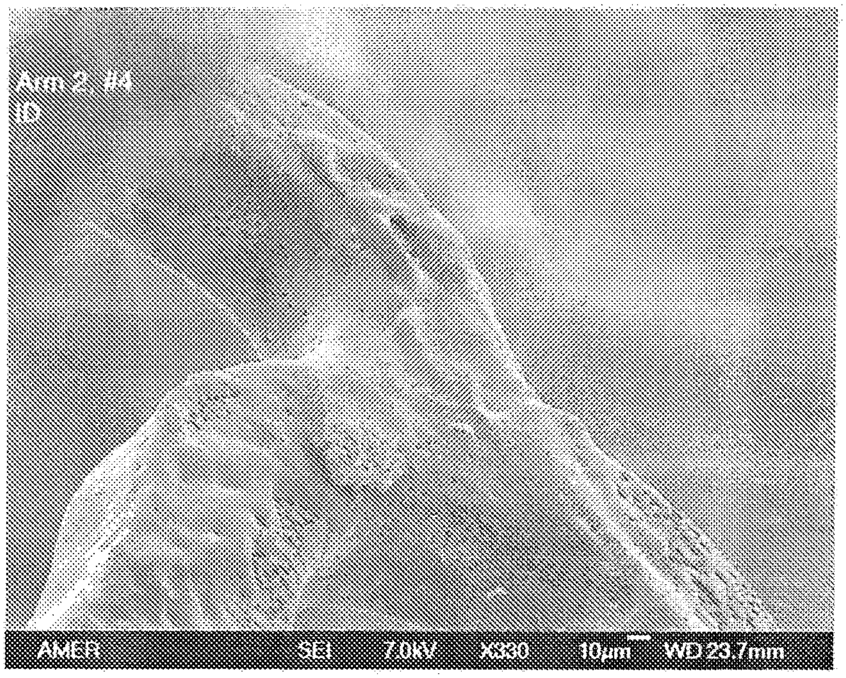
Figure 5:
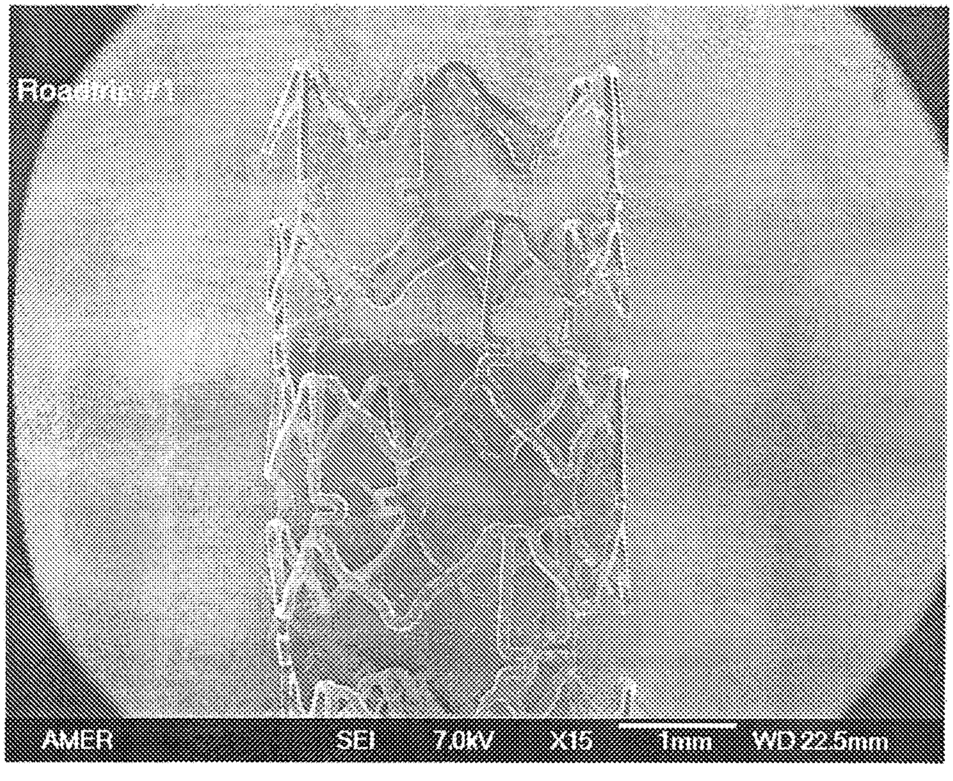
Figure 6:
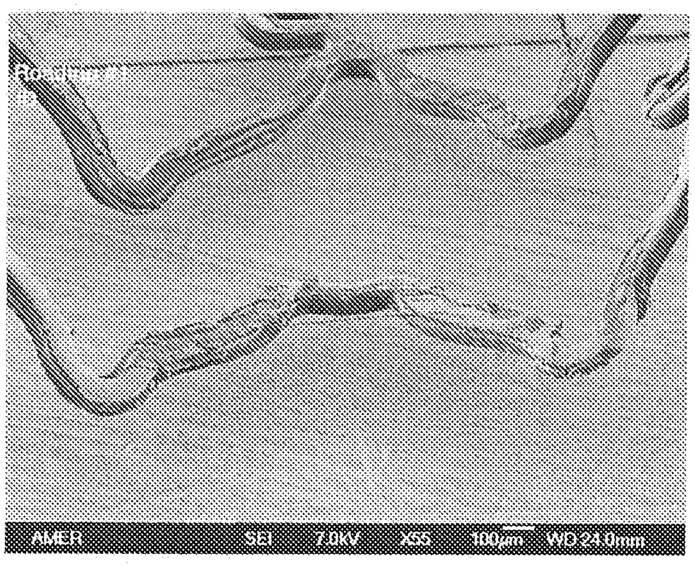

The stents were then microphotographed and compared with the control stent. The microphotographs showing different areas of the first stent having about 6 μg of sucrose applied over the PEA coating are shown by FIGS. 1 and 2; the microphotographs showing different areas of the second stent having about 64 μg of sucrose applied over the PEA coating are shown by FIGS. 3 and 4, and the microphotographs showing different areas of the control stent are shown by FIGS. 5 and 6. As can be seen from the comparison of the microphotographs, the sucrose layers on both the first and second stents provide protection against the sheer stress exerted over the stent coating by the expanding balloon. As a result, the PEA coating on both the first and the second stent are appreciably less damaged than the PEA coating on the control stent.

Example 2

Two separate coating formulations were prepared. The first balloon coating formulation ("the SOLEF® formulation") comprised a solution of about 2 mass % SOLEF® 21508, and the balance, a solvent blend containing acetone and cyclohexanone in a mass ratio of acetone to cyclohexanone of about 7:3. The second coating formulation ("the POLYACTIVE® formulation") comprised a solution of about 2 mass % POLYACTIVE® (300PEGT55PBT45) and the balance, a solvent blend containing trichloroethane and dimethylacetamide in a mass ratio of trichloroethane to dimethylacetamide of about 9:1. POLYACTIVE® contained units derived from ethylene glycol having molecular weight of about 300, and the ratio between the units derived from ethylene glycol and the units derived from butylene terephthalate was about 1.22:1. Four balloons of 12 mm VISION® catheters were coated according to the following procedure. The four catheters were cleaned using plasma treatment. For cleaning, the catheters were subjected to one cycle of 200 Watts 100% argon plasma, at a pressure of about 250 psi, and the temperature of about 25° C., for about 300 seconds. Following the plasma cleaning, the catheter balloons were inflated using a syringe. Stopcocks were used to prevent the deflation of the balloons.

Balloons #1 and #2 were then coated with the SOLEF® formulation by swabbing, while the balloons remained in the inflated state. To apply the SOLEF® formulation, the balloons were swiped twice with a sponge that was dipped in the first balloon coating formulation, followed by drying using a blow dryer set at medium heat (about 40-50° C.) and low speed for about 30 seconds. The dipping/swiping/drying procedure was repeated two more times; however, the blow dryer was set on medium heat and high speed for the third drying step. New sponges were used for each catheter balloon that was coated. The coating was then dried at about 60° C. for about 30 minutes in a convection oven. As a result, about 200 μg of SOLEF® 21508 was deposited on each balloon. The balloons remained inflated during the drying step to prevent adhering balloon pleats together. After the balloon coatings were dried, the stopcocks were removed, and the balloons #1 and #2 were refolded into their original configuration. Balloons #3 and #4 were then coated with the POLYACTIVE® formulation. The same coating procedure was used as for the coating of balloons #1 and #2. Next, two PEA-coated stents were crimped on catheters having coated balloons #1 and #2, and two PEA-coated stents were crimped on catheters having coated balloons #3 and #4, followed by electronic beam sterilization.

Figure 7:
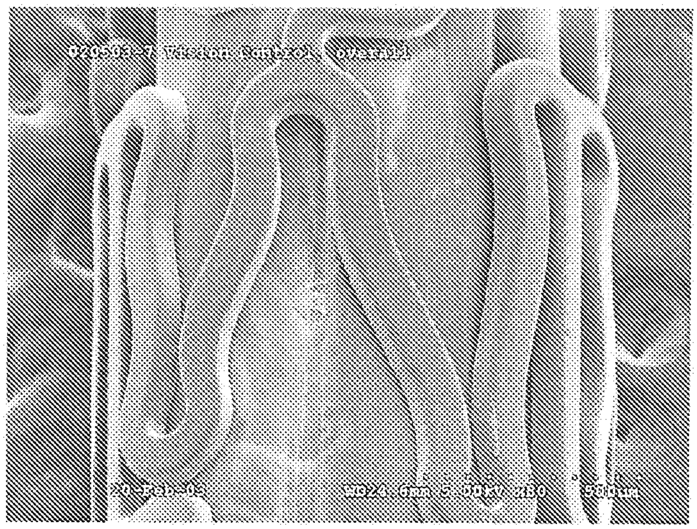
Figure 8:

As for the control assemblies, four 12 mm VISION® stents were coated with a PEA coating as described in Example 1. The coated stents were crimped on uncoated 12 mm VISION® catheters according to standard technique known to those having ordinary skill in the art. Micrographs shown by FIGS. 7 and 8 reveal that there are no visible areas where the stent coating adhered to the balloon and the overall quality of the coating was good with no apparent crimping damage. The control assemblies included the following stent/catheter assemblies:

(1) a PEA coated stent/uncoated catheter assembly; electronic beam-sterilized;

(2) a PEA coated stent/uncoated catheter assembly; electronic beam-sterilized;

(3) a PEA coated stent/uncoated catheter assembly; non-sterilized; and (4) a PEA coated stent/uncoated catheter assembly; ethylene oxide-sterilized.

All stent/balloon assemblies were then subjected to a simulated use test described in Example 1. The units were expanded to 16 atm in a PVA lesion. The balloon pressure was held at 16 atm for 1 minute after which the balloons were deflated and the catheter retracted to withdraw the balloon. In some cases, the stents were removed post-deployment rather than having water pumped through them for 1 hour per simulated use protocol.

Figure 9:
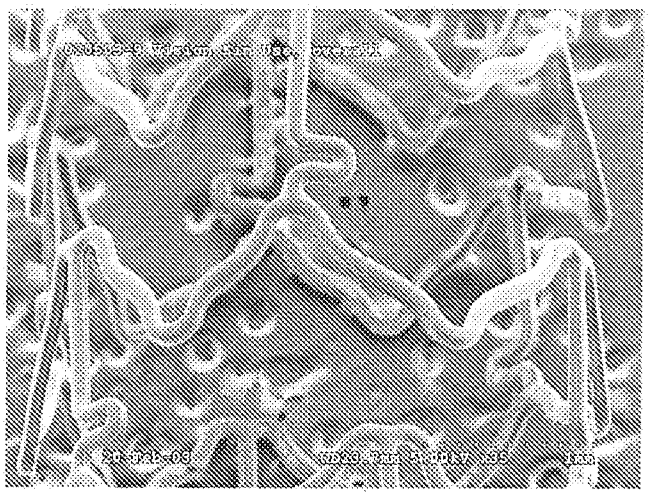
Figure 10:
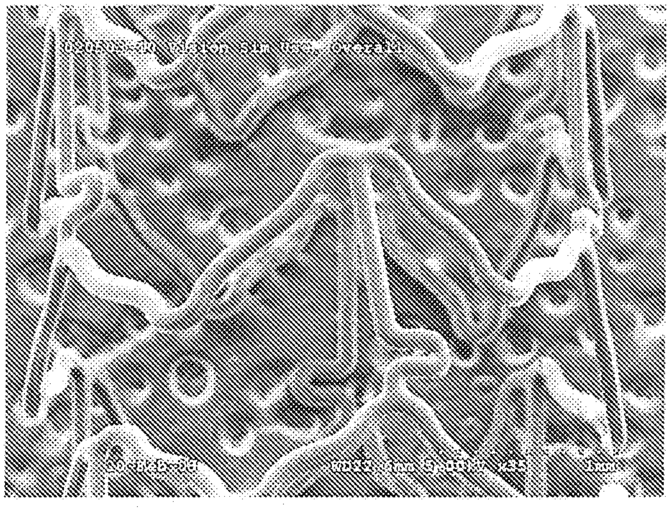
Figure 11:
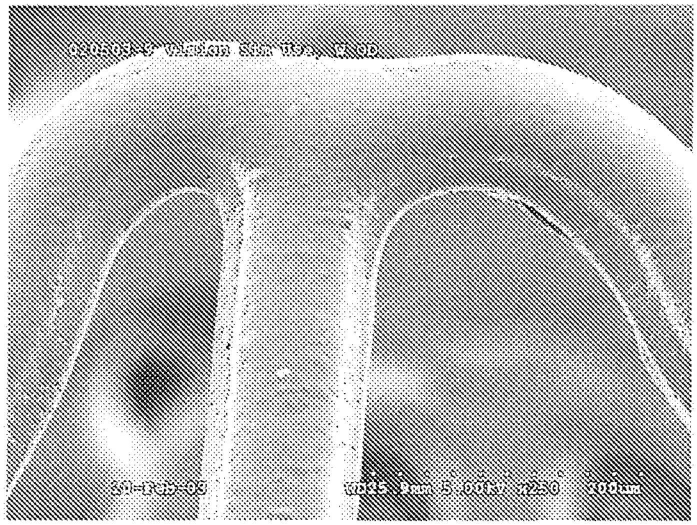
Figure 12:
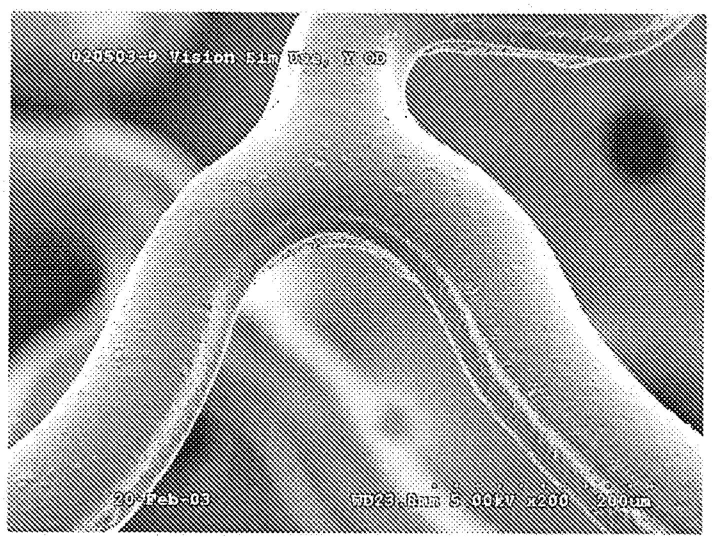
Figure 13:
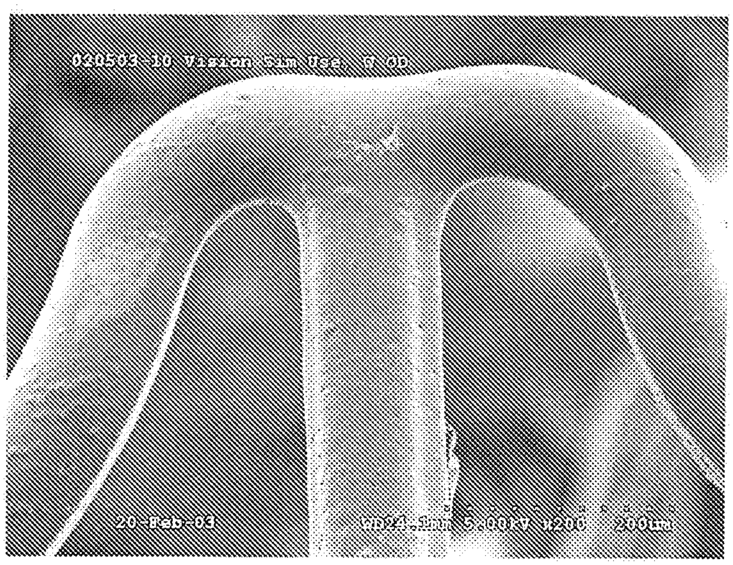
Figure 14:
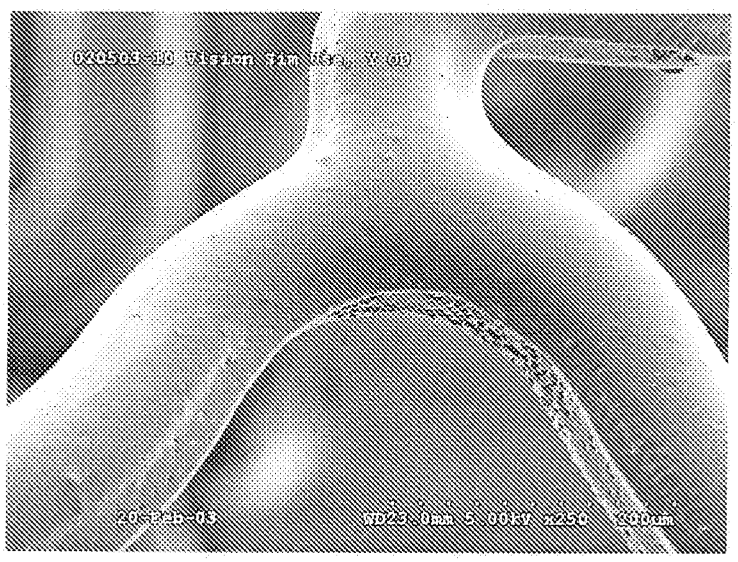
Figure 15:
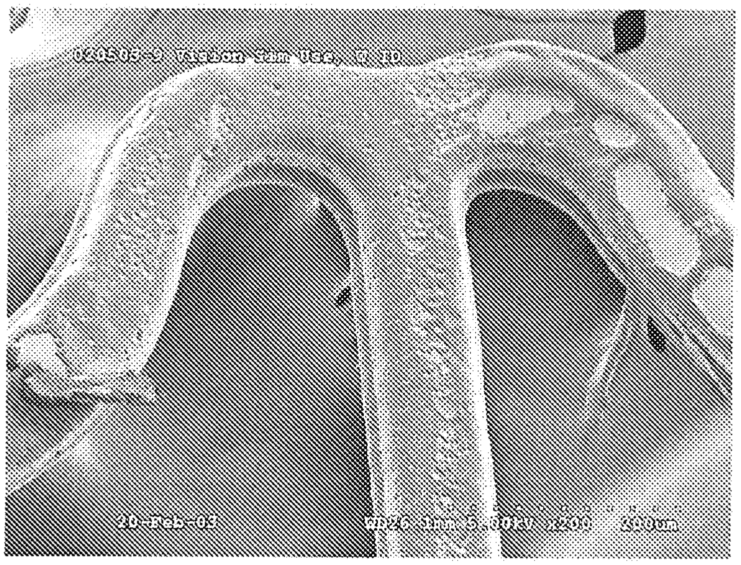
Figure 16:
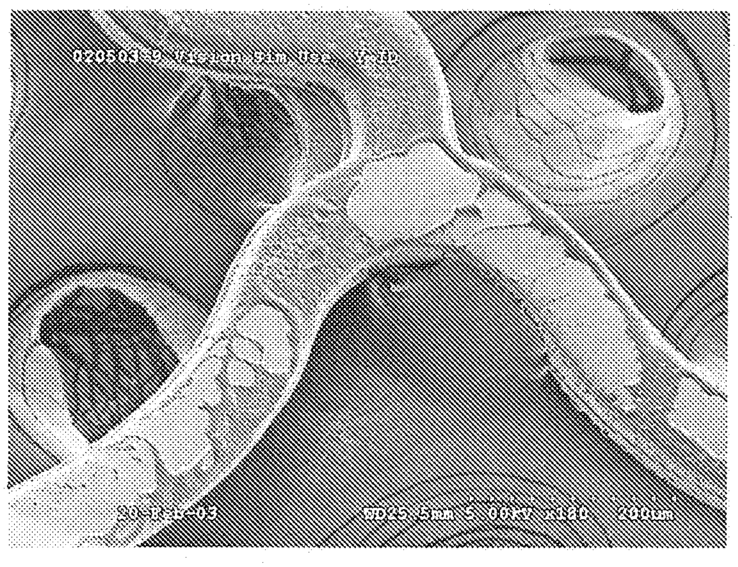
Figure 17:
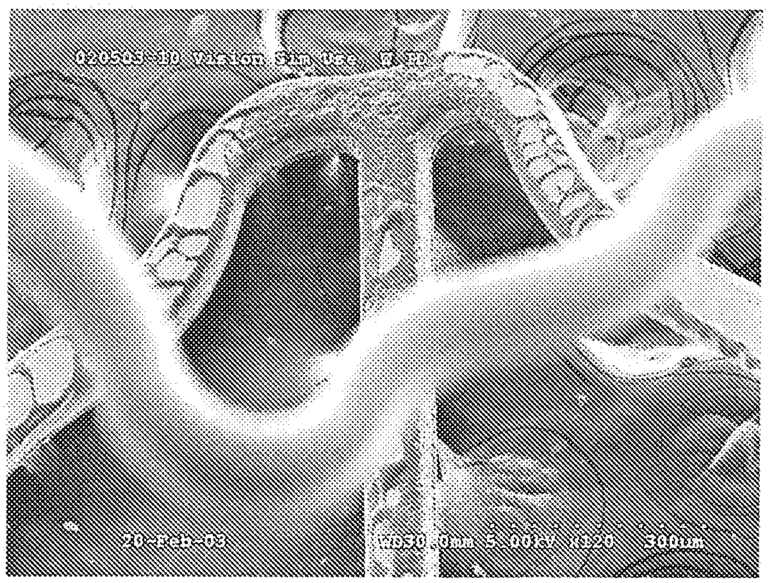
Figure 18:
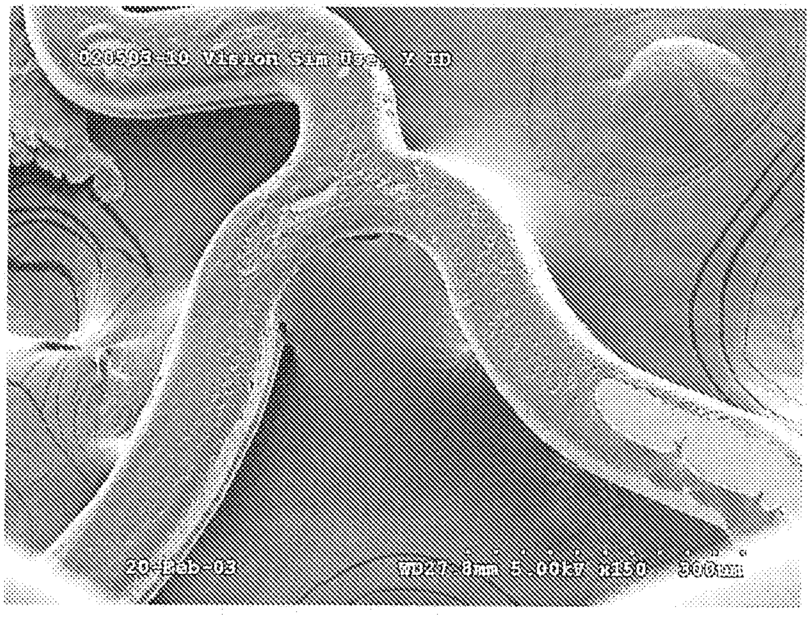

Overall views of the two stents of the control group expanded after deployment using coated stent/uncoated, electronic beam-sterilized catheter assemblies are shown by FIGS. 9 and 10. The quality of coatings on the outer surface areas of the stents after the simulated use test is illustrated by FIGS. 11-14. On the inner surface areas of the stents, a total failure of the coatings was observed, as shown by FIGS. 15, 16, 17, and 18. The microphotographs shown by FIGS. 15-18 indicate that the reason for the failure of the coatings was either adhesion between poly(ester amide) coatings and the uncoated catheter balloons or the balloon kinetic shear. Likewise, a substantial sheer damage was observed for the non-sterilized control assembly and for the ethylene oxide-sterilized assembly (not shown).

Figure 19:
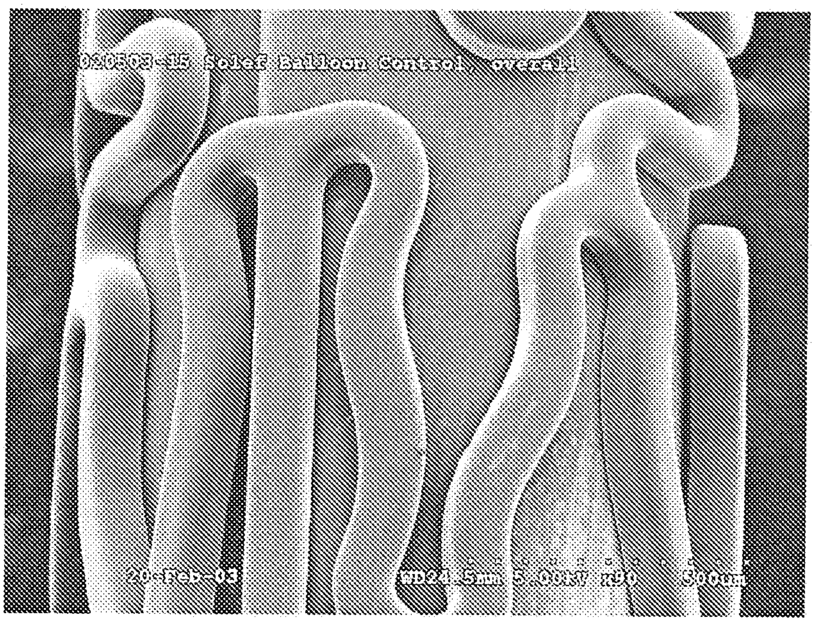
Figure 20:
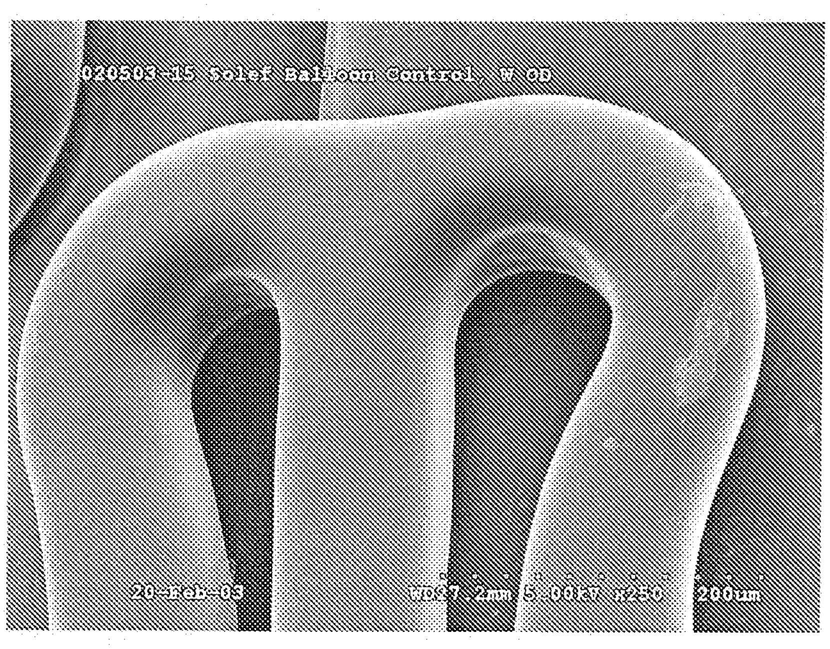
Figure 21:
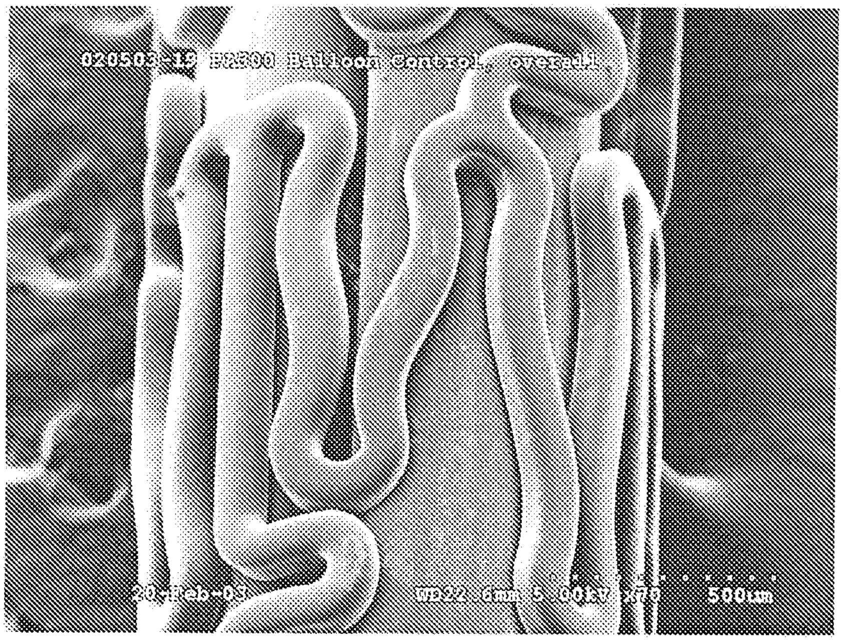
Figure 22:
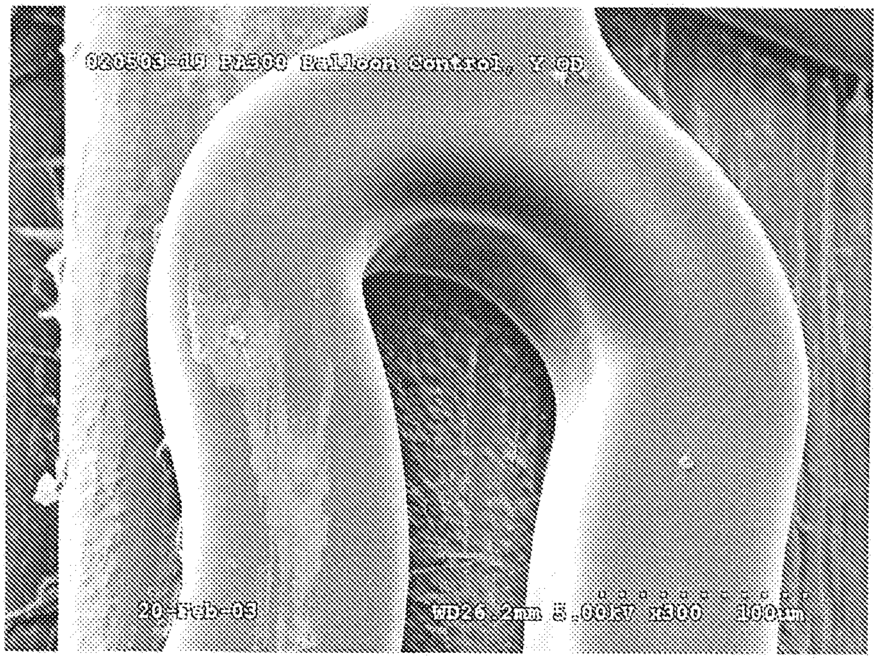

Turning now to the results of the simulated use test of the assemblies having SOLEF® coated balloons #1 and #2 ("group 1 assemblies") and the POLYACTIVE® coated balloons #3 and #4 ("group 2 assemblies"), microphotographs shown by FIGS. 19 and 20 (for group 1 assemblies) and FIGS. 21 and 22 (for group 2 assemblies) demonstrate that, prior to the test, the quality of the stents coatings in both groups was good with no apparent crimping damage and no visible areas where the stents coatings adhere to the balloon.

Figure 23:
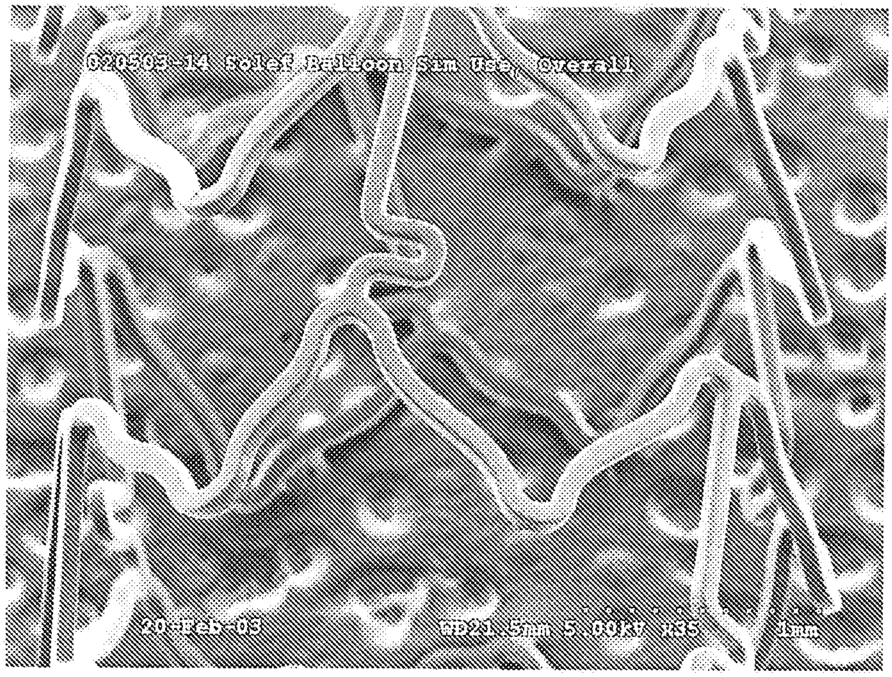
Figure 24:
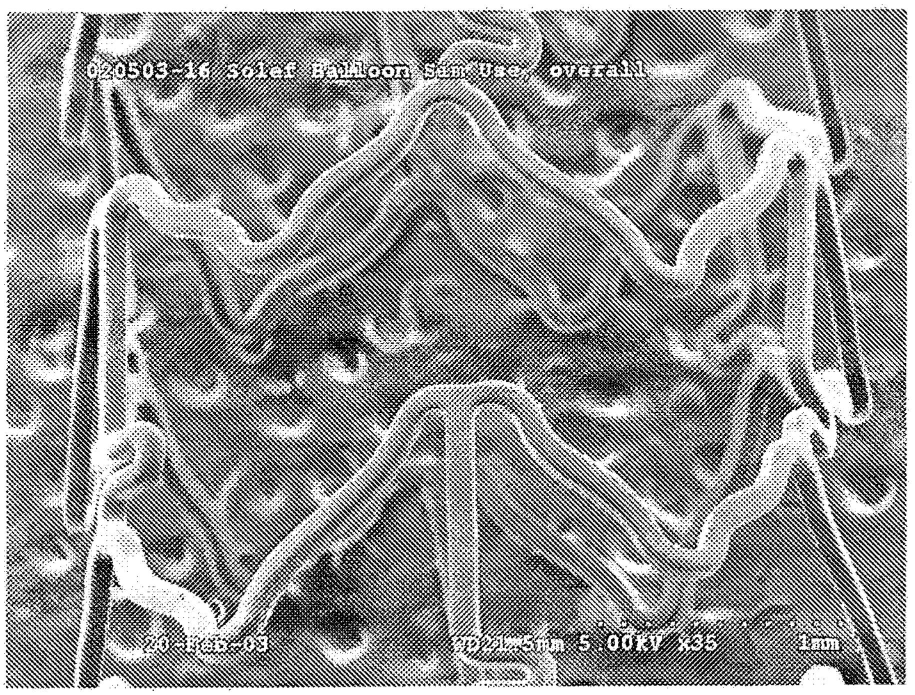
Figure 25:
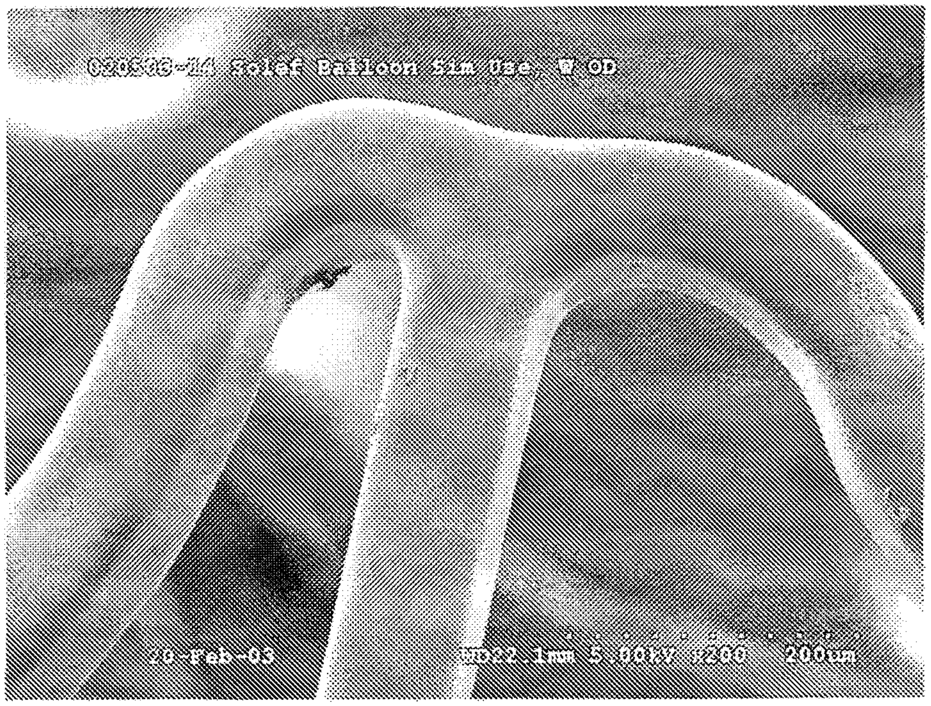
Figure 26:
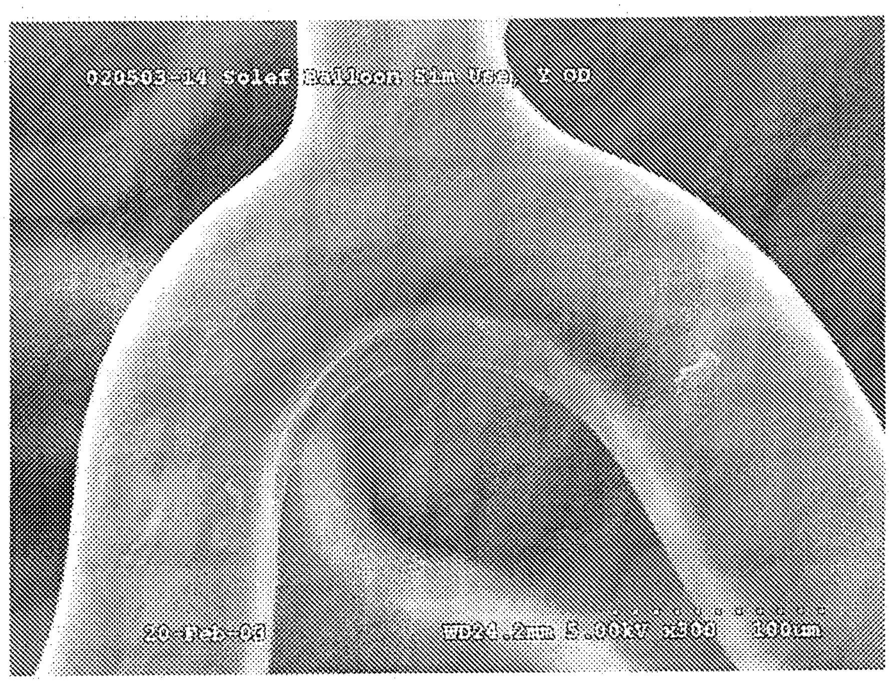
Figure 27:
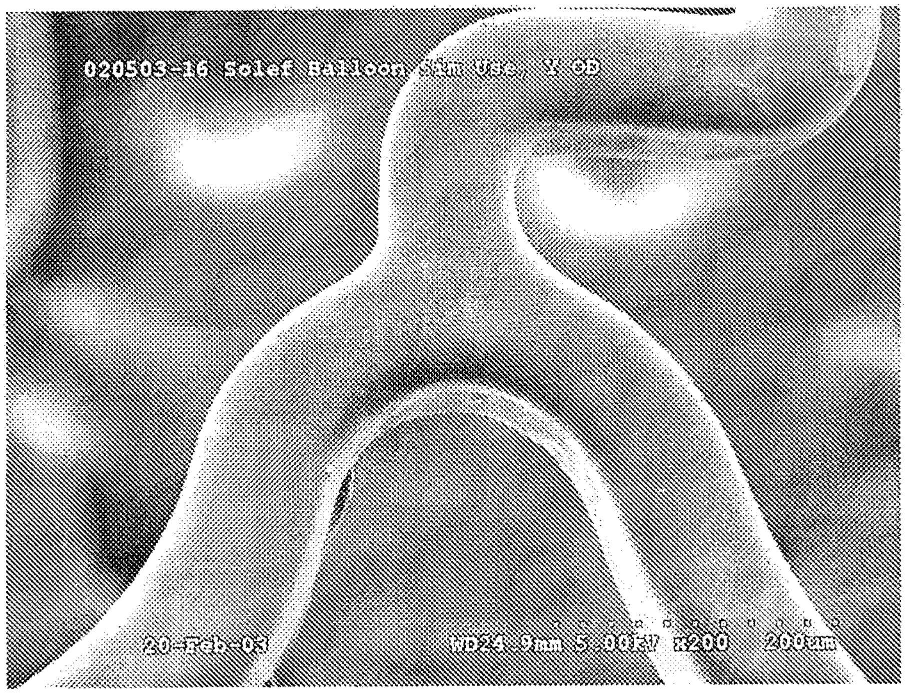
Figure 28:
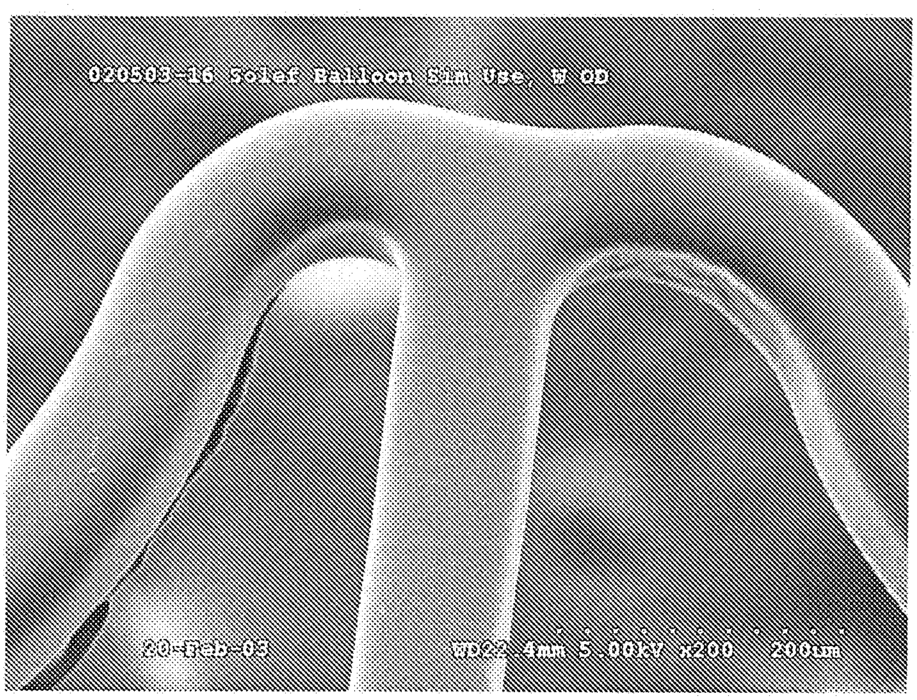
Figure 29:
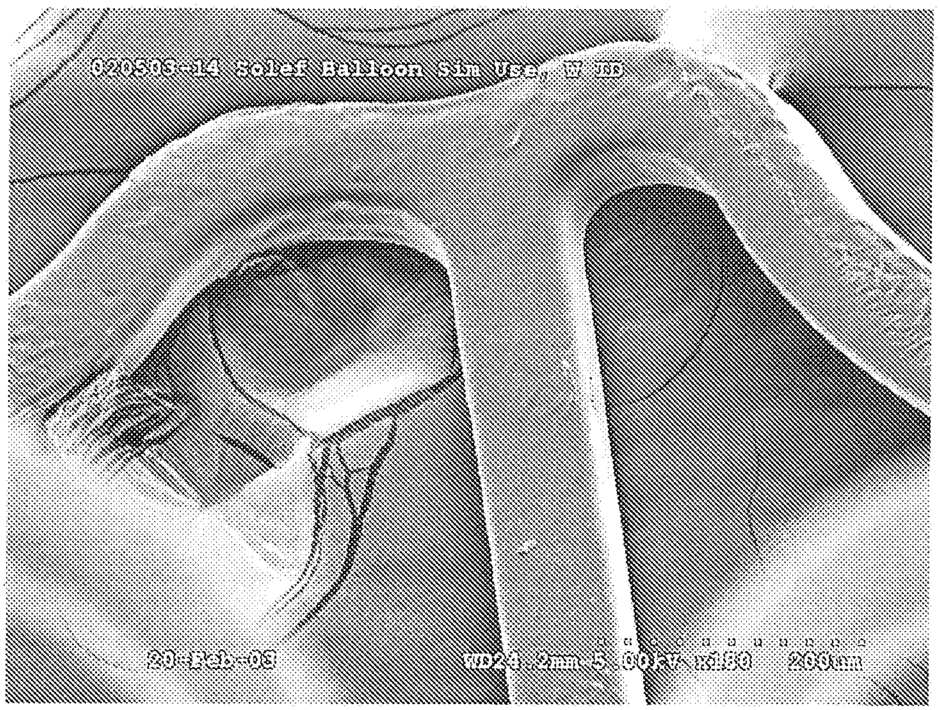
Figure 30:
Figure 31:
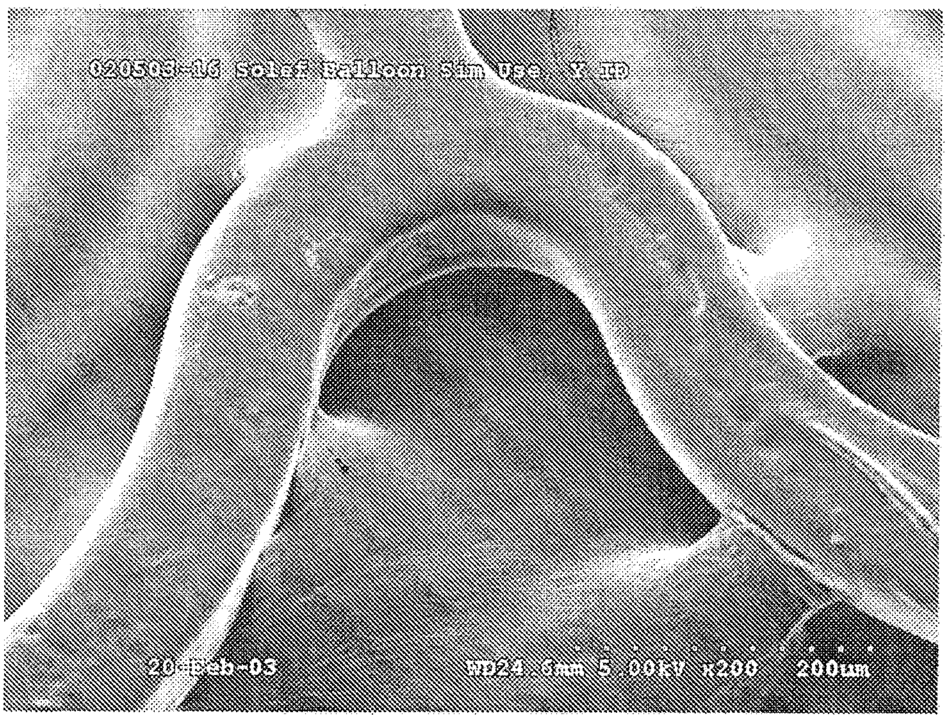
Figure 32:

Overall views of the stents of the group 1 assemblies expanded after deployment are shown by FIGS. 23 and 24. The quality of stents coatings after the simulated use test is illustrated by FIGS. 25-28 (only deployed in the simulated use apparatus). The damage of the coatings on the inner surface areas was only minimal, and the mechanical integrity of the coatings on the inner surface areas was largely preserved, as evidenced by FIGS. 29, 30, 31, and 32. Indeed, only a minimal coating movement on the inner surface area was observed as shown by FIGS. 29, 30 and 31. Just 3 to 4 tiny rips were observed in the coating on the inner surface area (FIG. 32), most likely caused by the spray mandrel during processing. Overall quality of the coatings on the inner surface area remained satisfactory.

Figure 33:
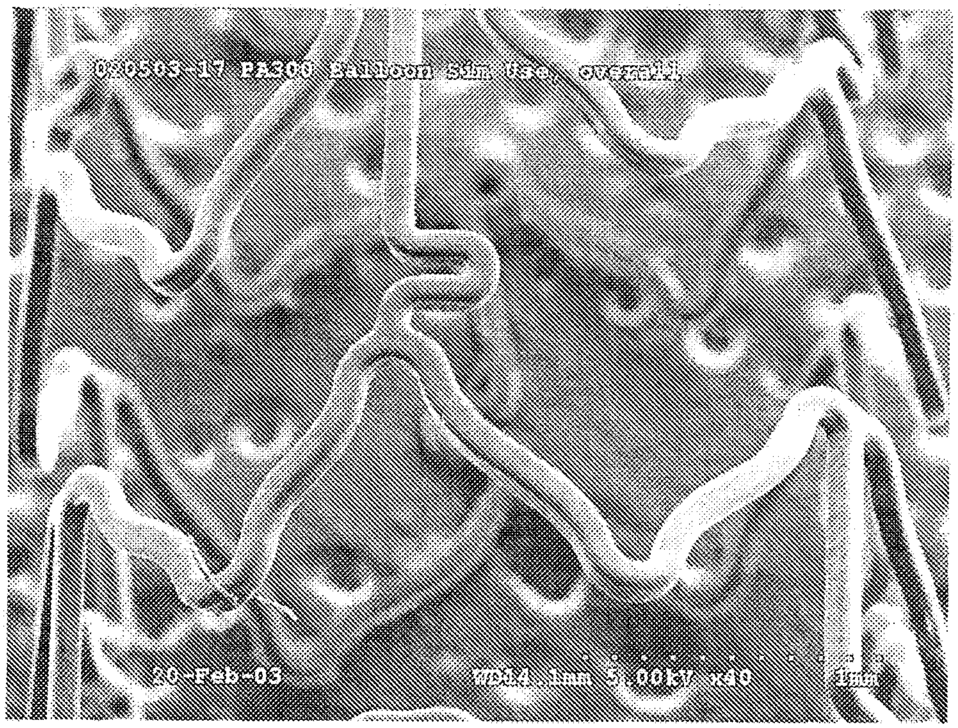
Figure 34:
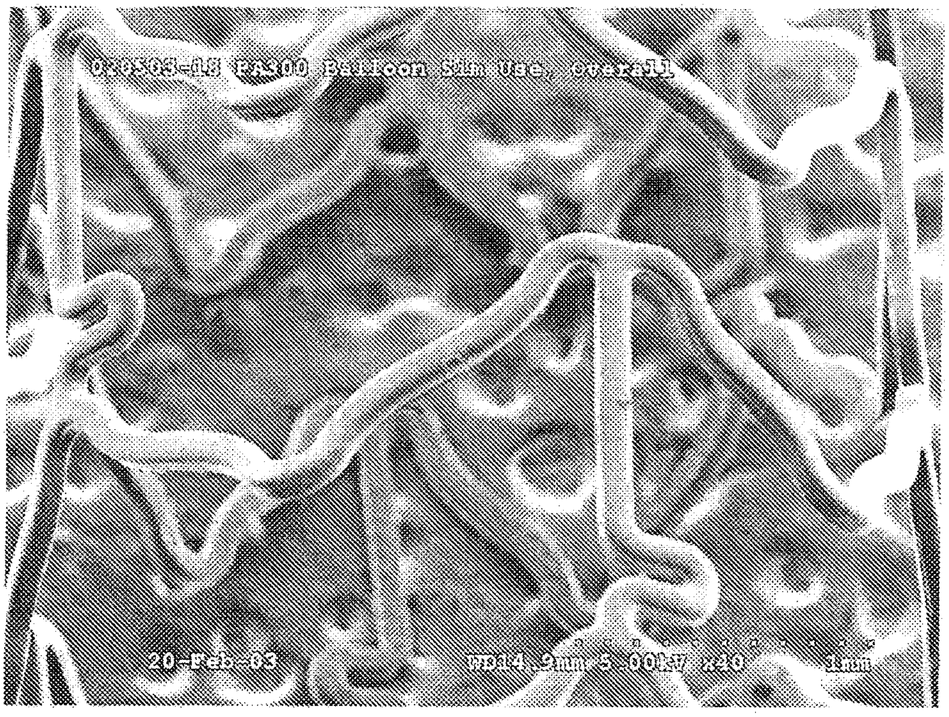
Figure 35:
Figure 36:
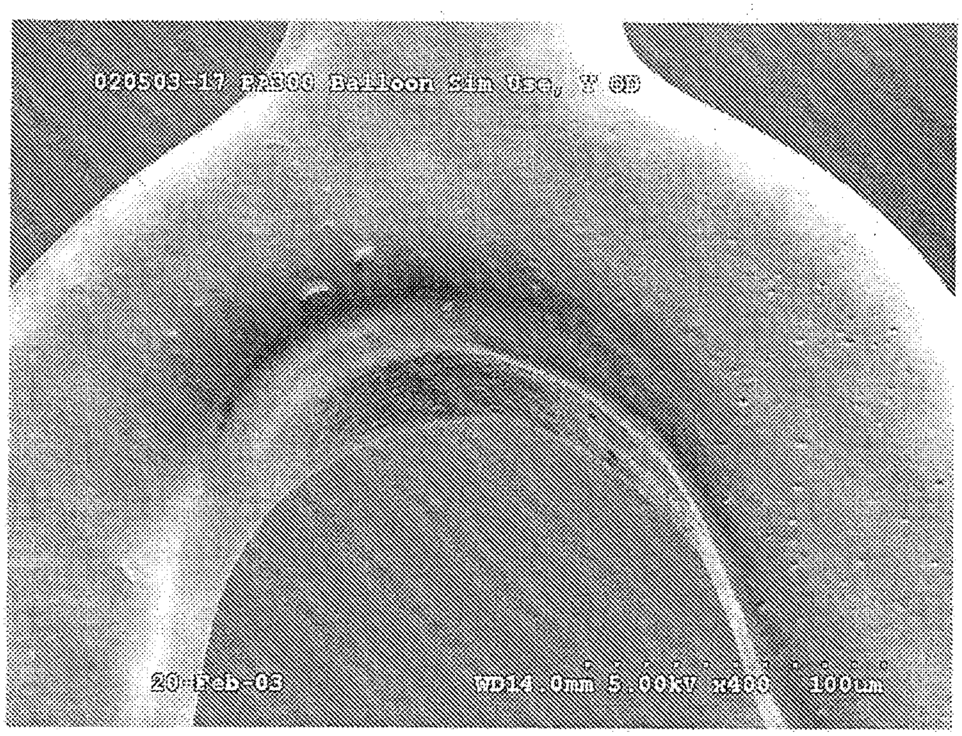
Figure 37:
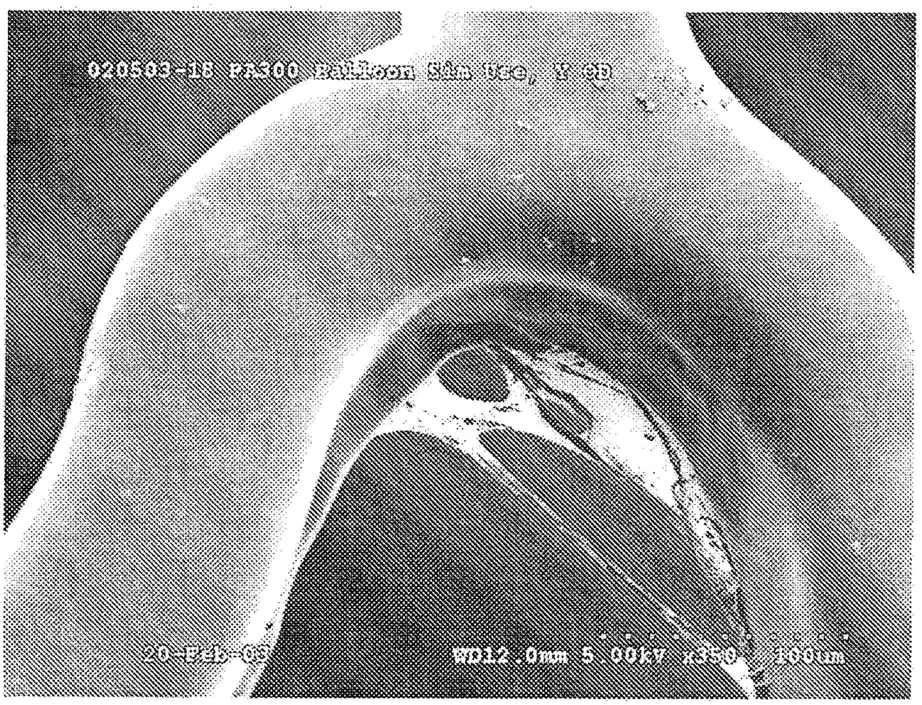
Figure 38:
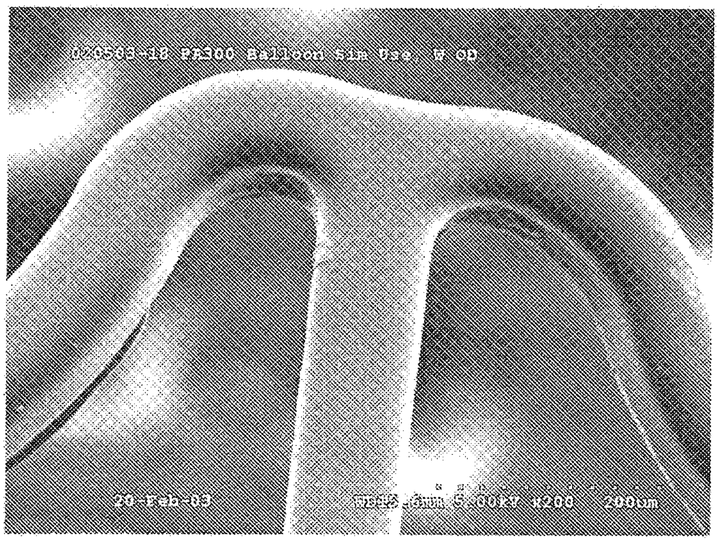
Figure 39:
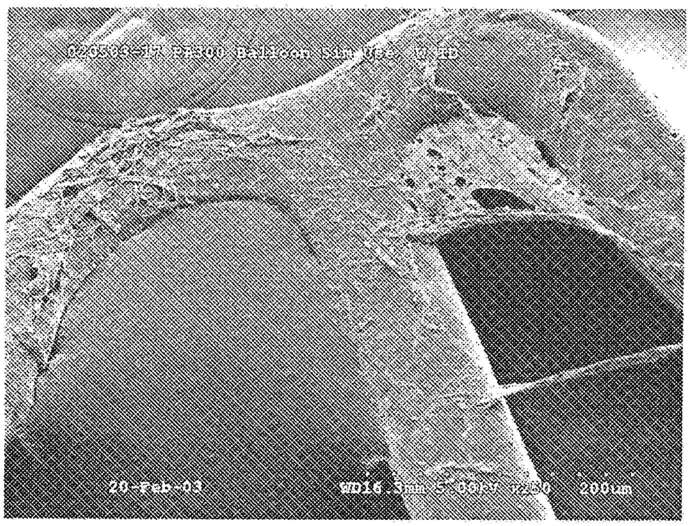
Figure 40:
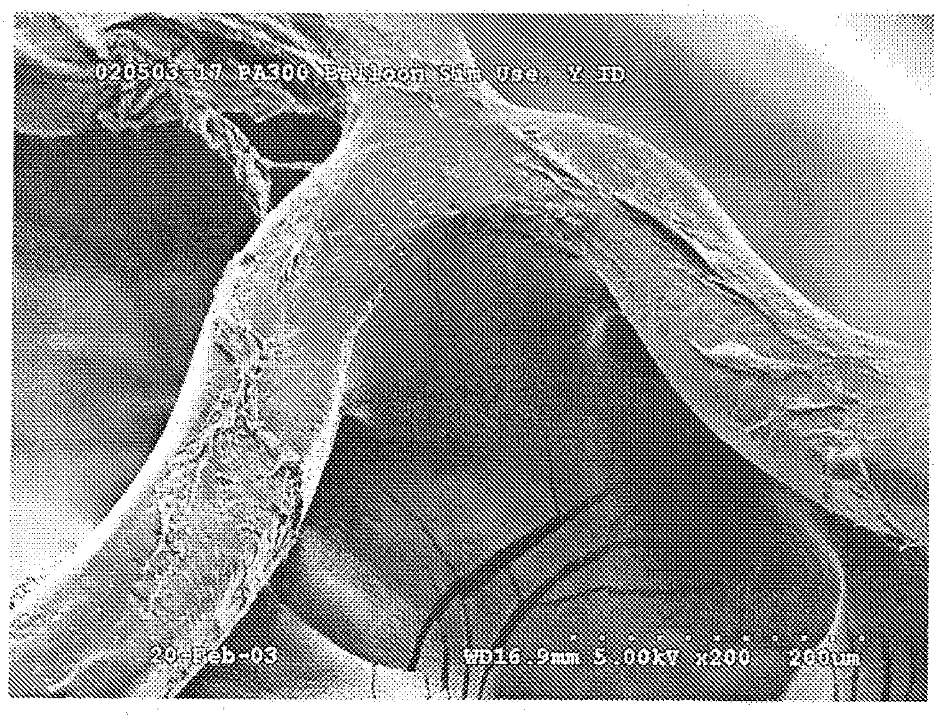
Figure 41:
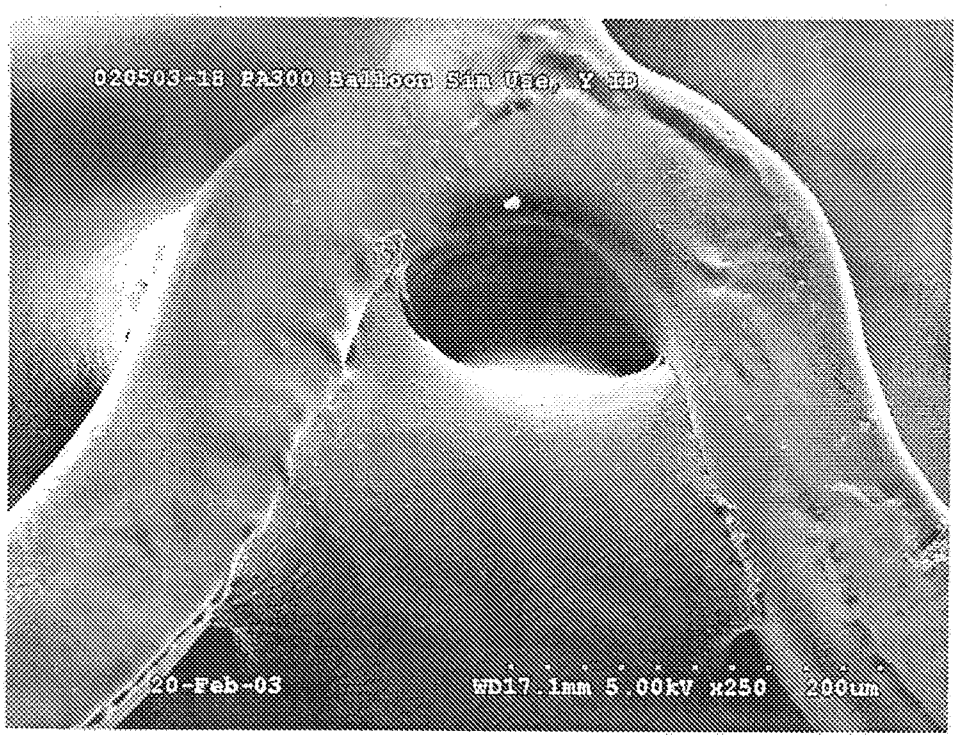
Figure 42:
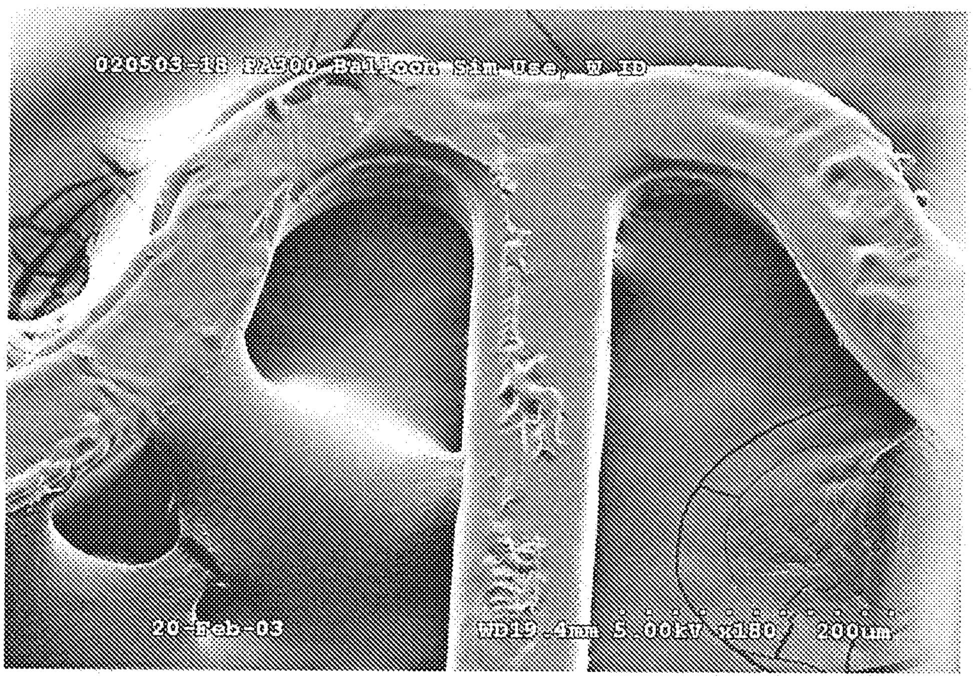

Turning to the group 2 assemblies, overall views of the stents, expanded after deployment, are shown by FIGS. 33 and 34. The quality of stents coatings after the simulated use test is illustrated by FIGS. 35-38 (only deployed in the simulated use apparatus). Although some delamination of the balloon coating was observed (FIGS. 37, 39, and 40), the stents' coating integrity is improved (FIGS. 41 and 42), as compared to the control group.

Example 3

A first composition was prepared by mixing about 2 mass % PEA; about 0.67 mass % everolimus; and the balance, 200 proof ethanol. The first composition was applied on four 12 mm VISION® stents as described in Example 1, and dried, to form a drug-polymer layer on each stent. The drug-polymer layer on each stent contained about 107 μg of everolimus and about 428 μg of PEA. A second composition, a 2% solution of PEA in 200 proof ethanol, was prepared and applied over the dried drug-polymer layer of each stent to form a topcoat layer. The topcoat layer on each stent contained about 300 μg of PEA. Each coated stent was crimped on an uncoated 12 mm VISION® catheter, to form stent/catheter assemblies. Two stent/catheter assemblies were then sterilized by electronic beam; the other two assemblies remained non-sterilized.

As a control group, four other catheter/stent assemblies were made. PEA coating containing no everolimus was formed on the stents. The PEA coating on each stent of the control group was made from a 2% solution of PEA in 200 proof ethanol. Two of the control assemblies were electronic-beam sterilized and the other two remained non-sterilized.

Figure 43:
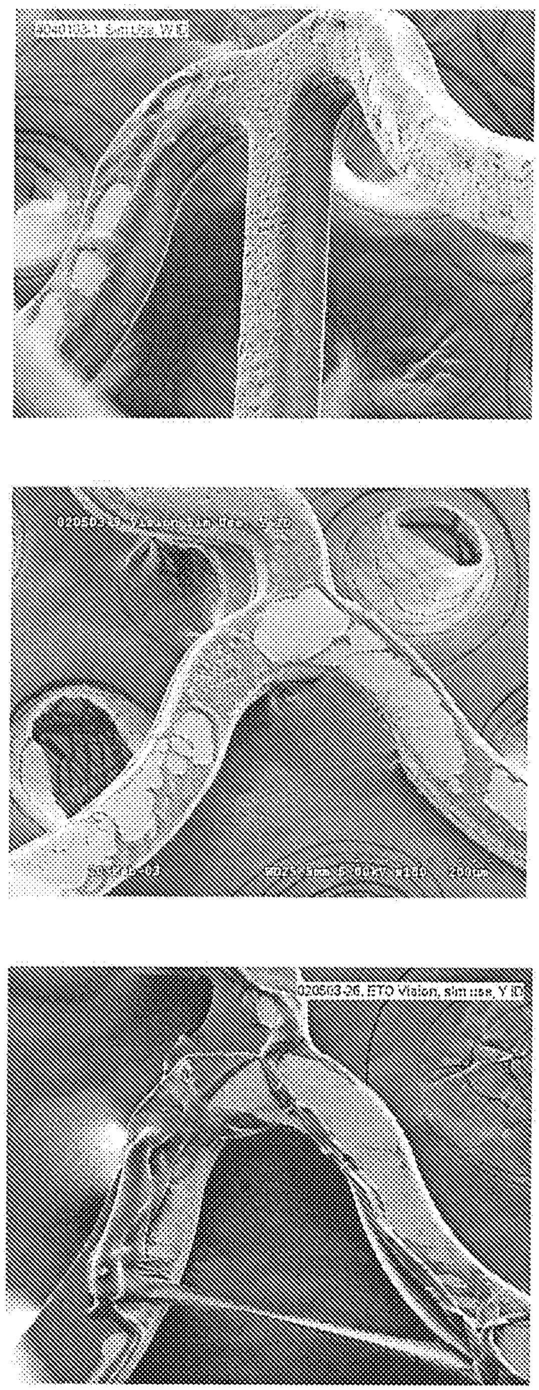
Figure 44:
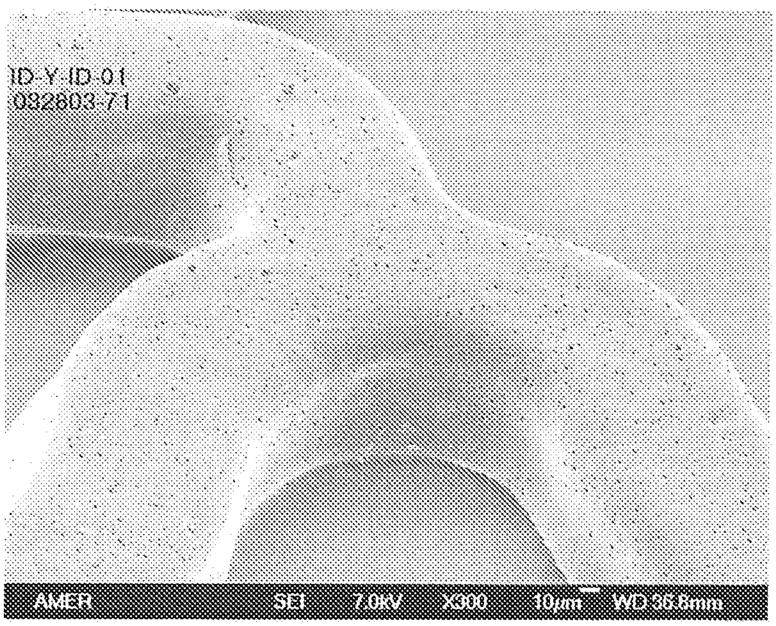

The eight assemblies were then subjected to the simulated use test described above. The test results are represented by FIGS. 43 and 44. The view of the inner surface area of a non-sterilized stent of the control group after deployment is shown by FIG. 43(*a*); the view of the inner surface area of a sterilized stent of the control group after deployment is shown by FIG. 43(*b*). After the simulated use test, the quality of coating on both the non-sterilized and sterilized control stents was poor, with the inner surface areas of the stents showing a total failure of the coating. In one additional experiment, a stent/catheter assembly was sterilized using ethylene oxide instead of electronic beam; however, the coating still failed after the simulated use test, as shown by FIG. 43(*c*).

Figure 45:
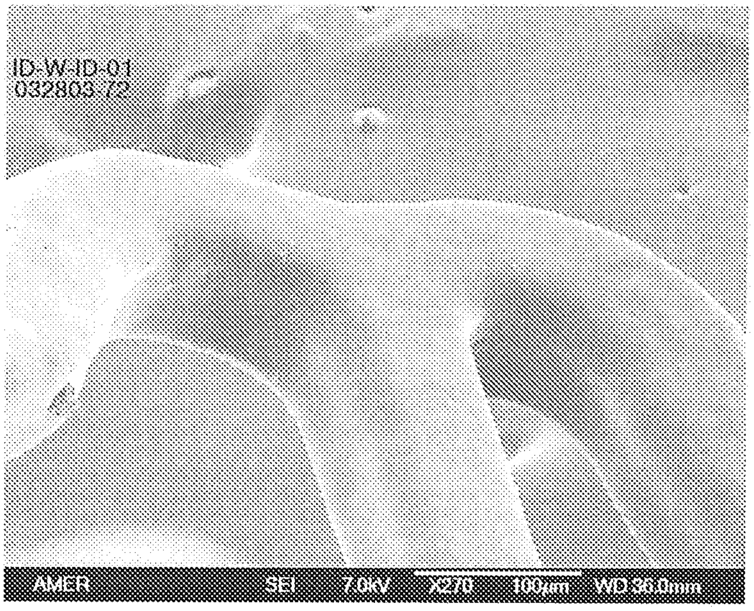
Figure 46:
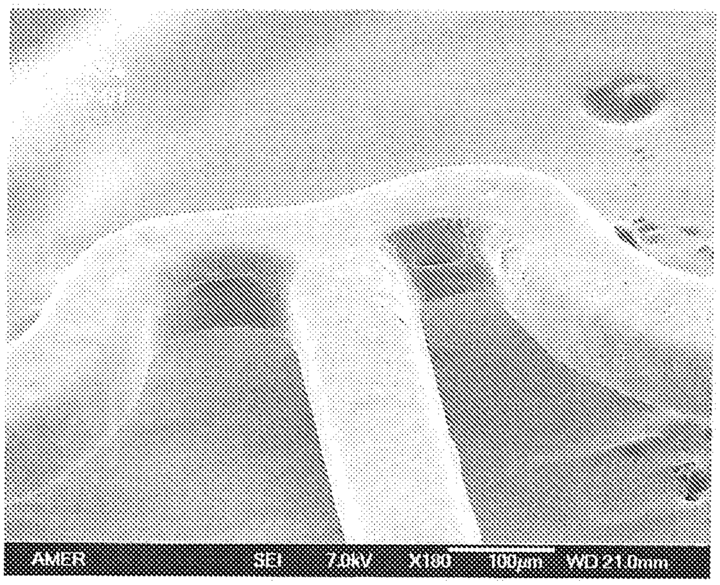

After the simulated use test on both the non-sterilized (FIGS. 44 and 45) and electronic-beam sterilized stent/catheter assemblies (FIG. 46), where the stent coatings contained everolimus, the quality of the stent coatings was substantially better as compared to the control group stents. The improvement can be appreciated by comparing FIG. 43(*a*) with FIGS. 44 and 45, and by comparing FIG. 43(*b*) with FIG. 46. The damage of the coatings on the inner surface areas was only minimal, and the mechanical integrity of the coatings on the inner surface areas was largely preserved.

Example 4

A first composition was prepared by mixing about 2 mass % PEA and the balance 200 proof ethanol. The first composition was applied on two 12 mm VISION® stents using the spraying technique described in Example 1, and dried, to form a PEA layer on each stent. The PEA layer on each stent contained about 100 μg of PEA. A second composition was prepared by mixing about 2 mass % everolimus and the balance 200 proof ethanol. The second composition was applied over the dry PEA layer of each stent and dried at room temperature. The drug layer on each stent contained about 107 μg of everolimus. A third composition was prepared by mixing about 2 mass % PEA and the balance 200 proof ethanol. The third composition was applied over the dry drug layer on each stent and dried. The topcoat layer on each stent contained about 300 μg of PEA.

Figure 47:
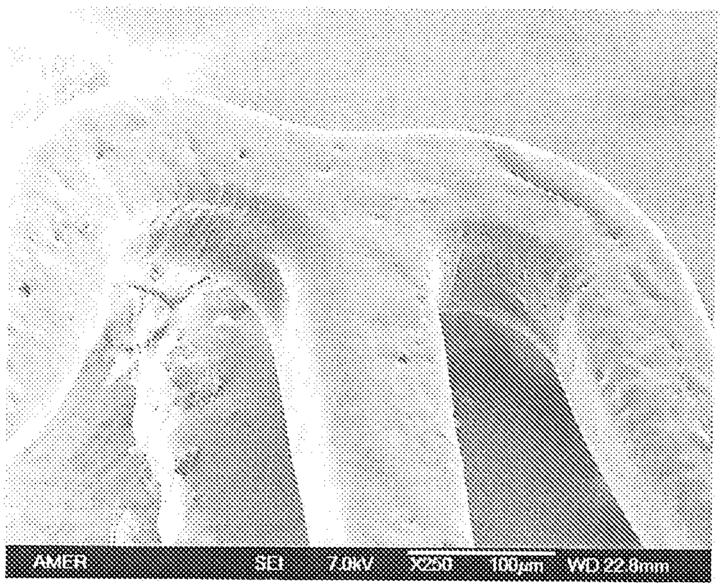
Figure 48:
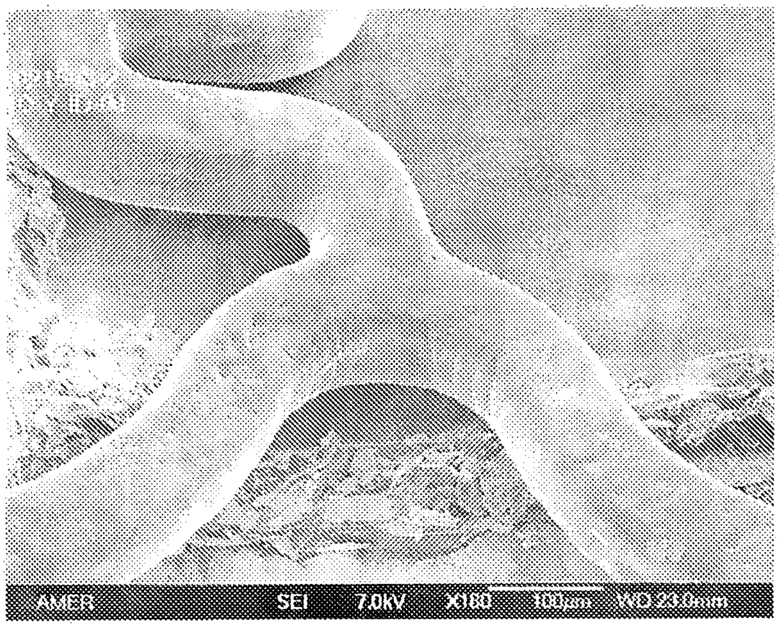

Each coated stent was crimped on an uncoated 12 mm VISION® catheter to form two stent/catheter assemblies. The stent/catheter assemblies were then sterilized by electronic beam and subjected to the simulated use test described above. After the simulated use test, the quality of the stents coatings, as shown by FIGS. 47 and 48, was substantially better compared with the control group stents shown by 43(*b*). The damage of the coatings on the inner surface areas was only minimal, and the mechanical integrity of the coatings on the inner surface areas was largely preserved.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of reducing adhesion and/or friction between a balloon of a catheter and a polymer coated stent in a medical assembly, the method comprising:

applying a solution consisting essentially of one or more blocking agents and a solvent or a mixture of solvents over a surface of the polymer coated stent to modify the surface, or over a surface of the balloon to modify the surface;

wherein the polymer coated stent comprises an active agent;

removing the solvent(s);

after removal of the solvent(s), crimping the polymer coated stent onto the balloon of the catheter to form the medical assembly;

wherein the one or more blocking agents are independently selected from the group consisting of block copolymers of bioabsorbable polymers with perfluorinated end chains, SILWET surfactants, FLUORAD surfactants, non-ionic surfactants having silicone chains, mono-, di-, and triglycerides, cholesterol, lecithin, dextran, and combinations thereof.

2. The method of claim 1, wherein the active agent is selected from the group consisting of clobetasol, estradiol, dexamethasone, paclitaxel, rapamycin, everolimus, 40-O-(3-hydroxy)propyl-rapamycin, 40-O-[2-(2-hydroxy)ethoxy]ethyl-rapamycin, 40-O-tetrazole-rapamycin, actinomycin D, docetaxel, methotrexate, azathioprine, vincristine, vinblastine, fluorouracil, doxorubicin, hydrochloride, mitomycin, sodium heparin, hirudin, argatroban, forskolin, vapiprost, prostacyclin, D-phe-pro-arg-chloromethylketone (synthetic antithrombin), dipyridamole, angiopeptin, captopril, cilazapril, lisinopril, nifedipine, colchicine, nitroprusside, suramin, permirolast potassium, tacrolimus, and combinations thereof.

3. The method of claim 2, wherein the one or more blocking agents are independently selected from the group consisting of SILWET surfactants, FLUORAD surfactants, and combinations thereof.

4. The method of claim 3, wherein the active agent is selected from the group consisting of clobetasol, estradiol, dexamethasone, paclitaxel, rapamycin, everolimus, 40-O-(3-hydroxy)propyl-rapamycin, 40-O-[2-(2-hydroxy)ethoxy]ethyl-rapamycin, 40-O-tetrazole-rapamycin, actinomycin D, docetaxel, captopril, cilazapril, lisinopril, nifedipine, tacrolimus, and combinations thereof.

5. The method of claim 2, wherein the one or more blocking agents are independently selected from the group consisting of mono-, di-, and triglycerides, cholesterol, lecithin, dextran, and combinations thereof.

6. The method of claim 5, wherein the active agent is selected from the group consisting of clobetasol, estradiol, dexamethasone, paclitaxel, rapamycin, everolimus, 40-O-(3-hydroxy)propyl-rapamycin, 40-O-[2-(2-hydroxy)ethoxy]ethyl-rapamycin, 40-O-tetrazole-rapamycin, actinomycin D, docetaxel, captopril, cilazapril, lisinopril, nifedipine, tacrolimus, and combinations thereof.

7. The method of claim 2, wherein the one or more blocking agents are independently selected from the group consisting of block copolymers of bioabsorbable polymers with perfluorinated end chains, non-ionic surfactants having silicone chains, and combinations thereof.

8. The method of claim 7, wherein the active agent is selected from the group consisting of clobetasol, estradiol, dexamethasone, paclitaxel, rapamycin, everolimus, 40-O-(3-hydroxy)propyl-rapamycin, 40-O-[2-(2-hydroxy)ethoxy]ethyl-rapamycin, 40-O-tetrazole-rapamycin, actinomycin D, docetaxel, captopril, cilazapril, lisinopril, nifedipine, tacrolimus, and combinations thereof.

9. A method of reducing adhesion and/or friction between a balloon of a catheter and a polymer coated stent in a medical assembly, the method comprising:

applying a solution consisting essentially of one or more blocking agents and a solvent or a mixture of solvents over a surface of the polymer coated stent to modify the surface, or over a surface of the balloon to modify the surface;

removing the solvent(s);

after removal of the solvent(s), crimping the polymer coated stent onto the balloon of the catheter to form the medical assembly;

wherein the one or more blocking agents are independently selected from the group consisting of block copolymers of bioabsorbable polymers with perfluorinated end chains, SILWET surfactants, FLUORAD surfactants, non-ionic surfactants having silicone chains, mono-, di-, and triglycerides, cholesterol, lecithin, dextran, and combinations thereof.

10. The method of claim 9, wherein the one or more blocking agents are independently selected from the group consisting of SILWET surfactants, FLUORAD surfactants, and combinations thereof.

11. The method of claim 9, wherein the one or more blocking agents are independently selected from the group consisting of mono-, di-, and triglycerides, cholesterol, lecithin, dextran, and combinations thereof.

12. The method of claim 9, wherein the one or more blocking agents are independently selected from the group consisting of block copolymers of bioabsorbable polymers with perfluorinated end chains, non-ionic surfactants having silicone chains, and combinations thereof.

* * * * *